(12) United States Patent
Hua et al.

(10) Patent No.: US 6,727,277 B1
(45) Date of Patent: Apr. 27, 2004

(54) COMPOUNDS AFFECTING CHOLESTEROL ABSORPTION

(75) Inventors: Duy H. Hua, Manhattan, KS (US); Sung I. Koo, Storrs, CT (US); Sang K. Noh, Wrillimantic, CT (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 10/292,720

(22) Filed: Nov. 12, 2002

(51) Int. Cl.$^7$ .......................... A61K 31/35; C07C 43/20

(52) U.S. Cl. .................. 514/453; 549/214; 549/384; 568/633

(58) Field of Search .................. 514/453; 549/214, 549/384; 568/633

(56) References Cited

U.S. PATENT DOCUMENTS

| | | | |
|---|---|---|---|
| 5,003,076 A | 3/1991 | Narita et al. |
| 5,008,409 A | 4/1991 | Narisada et al. |
| 5,017,380 A | 5/1991 | Hamashima et al. |
| 5,017,708 A | 5/1991 | Ogata et al. |
| 5,041,635 A | 8/1991 | Narisada et al. |
| 5,047,574 A | 9/1991 | Ohtani et al. |
| 5,063,048 A | 11/1991 | Saitoh et al. |
| 5,064,473 A | 11/1991 | Kubo et al. |
| 5,089,043 A | 2/1992 | Hayase et al. |
| 5,091,569 A | 2/1992 | Matsumoto et al. |
| 5,117,039 A | 5/1992 | Ohtani et al. |
| 5,120,733 A | 6/1992 | Matsumura et al. |
| 5,120,865 A | 6/1992 | Narisada et al. |
| 5,134,077 A | 7/1992 | Sonoyama et al. |
| 5,137,914 A | 8/1992 | Ohtani et al. |
| 5,166,425 A | 11/1992 | Tsushima et al. |
| 5,175,186 A | 12/1992 | Barbier et al. |
| 5,175,341 A | 12/1992 | Ohtani et al. |
| 5,183,909 A | 2/1993 | Ohtani et al. |
| 5,200,533 A | 4/1993 | Narisada et al. |
| 5,202,345 A | 4/1993 | Matsumura et al. |
| 5,214,202 A | 5/1993 | Hamada et al. |
| 5,215,972 A | 6/1993 | Cassal et al. |
| 5,241,104 A | 8/1993 | Ohtani et al. |
| 5,246,960 A | 9/1993 | Barbier et al. |
| 5,250,705 A | 10/1993 | Okada et al. |
| 5,258,551 A | 11/1993 | Murabayashi et al. |
| 5,268,386 A | 12/1993 | Harada et al. |
| 5,281,525 A | 1/1994 | Mitsushima et al. |
| 5,322,928 A | 6/1994 | Yamashita et al. |
| 5,338,676 A | 8/1994 | Mitsushima et al. |
| 5,362,873 A | 11/1994 | Matsumura et al. |
| 5,407,929 A | 4/1995 | Takahashi et al. |
| 5,414,122 A | 5/1995 | Murabayashi et al. |
| 5,420,145 A | 5/1995 | Shudo |
| 5,459,064 A | 10/1995 | Teraoka et al. |
| 5,459,264 A | 10/1995 | Imuta et al. |
| 5,495,048 A | 2/1996 | Aebi et al. |
| 5,498,792 A | 3/1996 | Masumoto et al. |
| 5,510,506 A | 4/1996 | Takase et al. |
| 5,534,654 A | 7/1996 | Ohtani et al. |
| 5,539,102 A | 7/1996 | Sendo et al. |
| 5,563,264 A | 10/1996 | Kume et al. |
| 5,612,190 A | 3/1997 | Arita et al. |
| 5,629,442 A | 5/1997 | Takase et al. |
| 5,637,771 A | 6/1997 | Aebi et al. |
| 5,639,855 A | 6/1997 | Kitamura et al. |
| 5,665,586 A | 9/1997 | Nakamura et al. |
| 5,696,271 A | 12/1997 | Takada et al. |
| 5,760,244 A | 6/1998 | Takada et al. |
| 5,763,647 A | 6/1998 | Ohtani et al. |
| 5,830,703 A | 11/1998 | Kitamura et al. |
| 5,856,503 A | 1/1999 | Aebi et al. |
| 5,871,742 A | 2/1999 | Saitoh et al. |
| 5,910,416 A | 6/1999 | Kitamura et al. |
| 5,948,819 A | 9/1999 | Ohtsuka et al. |
| 6,111,098 A | 8/2000 | Inoue et al. |
| 6,313,150 B1 | 11/2001 | Ohtsuka et al. |
| 6,320,060 B1 | 11/2001 | Honma et al. |
| 6,384,045 B1 | 5/2002 | Hua et al. |

OTHER PUBLICATIONS

Amade et al., "A Dimer of Puupehenone," *Helv. Chim. Acta*, 1983, 66:1672–1675.

Arjona et al., "Total Synthesis of both Enantiomers of 15–Oxopuupehenol Methylendioxy Derivatives," *Tetrahedron Letters*, 1997, 38(41):7249–7252.

Barrero et al., "Enantiospecific Synthesis of (+)–Puupehenone from (−)–Sclareol and Protocatechualdehyde," *Tetrahedron Letters*, 1997, 38(12):2325–2328.

Barrero et al., "Enantiospecific Synthesis of Wiedendiol–B from (−)–Sclareol and (+)–cis–Abienol," *Tetrahedron Letters*, 1997, 38(46):8101–8104.

Barrero et al., "Synthesis of Wiedendiol–A and Wiedendiol–B from Labdane Diterpenes," *Tetrahedron*, 1998, 54:5635–5650.

(List continued on next page.)

*Primary Examiner*—Amelia Owens
(74) *Attorney, Agent, or Firm*—Fish & Richardson P.C., P.A.

(57) ABSTRACT

A class of novel compounds is described for use in affecting lymphatic absorption of cholesterol. Compounds of particular interest are defined by Formula I:

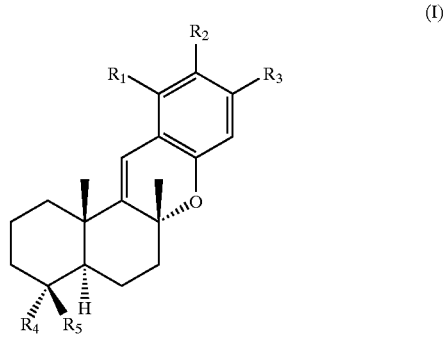

(I)

or a pharmaceutically acceptable salt thereof.

51 Claims, 4 Drawing Sheets

OTHER PUBLICATIONS

Barrero et al., "Synthesis and Antitumor Activity of Puupehedione and Related Compounds#," *Tetrahedron*, 1999, 55:15181–15208.

Chackalamannil et al., "An Efficient Synthesis of Wiedendiol–A from (+)–Sclareolide," *Tetrahedron Letters*, 1995, 36(30):5315–5318.

Coval et al., "Wiedendiol–A and–B, Cholesteryl Ester Transfer Protein Inhibitors from the Marine Sponge *Xestospongla Wiedenmayeri*," *Bioorg. Med. Chem. Lett.*, 1995, 5(6):605–610.

Detmers et al., "A target for cholesterol absorption inhibitors in the enterocyte brush border membrane," *Biochim. Biophys. Acta*, 2000, 1486:243–252.

El Sayed et al., "The Marine Environment: A Resource for Prototype Antimalarial Agents," *J. Natural Toxins*, 1996, 5(2):261–285.

Grundy, "Medical Intelligence Drug Therapy," *New Engl. J. Med.*, 1988, 319:24–33.

Hamann and Scheuer, "Cyanopuupehenol, an Antiviral Metabolite of a Sponge of the Order Verongida," *Tetrahedron Lett.*, 1991, 32(41):5671–5672.

Hamann and Scheuer, "Biogenetically Diverse, Bioactive Constituents of a Sponge, Order Verongida: Bromotyramines and Sesquitepene–Shikimate Derived Metabolites," *J. Org. Chem.*, 1993, 58:6565–6569.

Hann and Spencer, "The Preparation of Chlorovanillin and Some of its Derivatives," *J. Am. Chem. Soc.*, 1927, 49:535–537.

Jong et al.,"Total Synthesis and X–ray Structure Determination of Cyanobacterin,"*J. Org. Chem.*, 1984, 49:735–736.

Koo and Noh, "Phosphatidylcholine Inhibits and Lysophosphatidylcholine Enhances the Lymphatic Absorption of α–tocopherol in Adult Rats," *J. Nutr.*, 2001, 131:717–722.

Kritchevsky et al., "Influence of Conjugated Linoleic Acid (CLA) on Establishment and Progression of Atherosclerosis in Rabbits," *J. Am. Coll. Nutr.*, 2000, 19(4):472S–477S.

Kuivenhoven et al.,"The Role of a Common Variant of the Cholesteryl Ester Transfer Protein Gene in the Progression of Coronary Atherosclerosis," *New Engl. J. Med.*, 1998, 338:86–93.

Lee et al., "Conjugated linoleic acid and atherosclerosis in rabbits," *Atherosclerosis*, 1994, 108:19–25.

Löest et al., "Green Tea Extract Inhibits the Lymphatic Absorption of Cholesterol and α–Tocopherol in Ovariectomized Rats," *J. Nutr.*, 2002, 132:1282–1288.

Nasu et al., "Puupehenone–Related Metabolites from Two Hawaiian Sponges, *Hyritos* spp.," *J. Org. Chem.*, 1995, 60:7290–7292.

Nicolosi et al., "Dietary Conjugated Linoleic Acid Reduces Plasma Lipoproteins And Early Aortic Atherosclerosis In Hypercholesterolemic Hamsters," *Artery*, 1997, 22(5):266–277.

Popov et al.,"Antimicrobial and Cytotoxic Activity of Sesquiterpenequinones and Brominated Diphenyl Esters Isolated from Marine Sponges," *Pharm. Chem. J.*, 1999, 33(2):71–73.

Ravi et al., "Recent Research in Marine Natural Products: The Puupehenones," *Pure & Appl. Chem.*, 1979, 51:1893–1900.

Reeves et al., "AIN–93 Purified Diets for Laboratory Rodents: Final Report of the American Institute of Nutrition Ad Hoc Writing Committee on the Reformulation of the AIN–76A Rodent Diet," *J. Nutr.*, 1993, 123:1939–1951.

Reeves, "AIN–93 Purified Diets for the Study of Trace Element Metabolism in Rodents," *Trace Elements in Laboratory Rodents*, Watson (ed.), 1996, CRC Press, Boca Raton, FL, Chapter 1, pp. 3–37.

Ross, "The pathogenesis of atherosclerosis: a perspective for the 1990s," *Nature*, 1993, 362:801–809.

Scandinavian Simvastatin Survival Study Group, "Randomised trial of cholesterol lowering in 4444 patients with coronary heart disease: the Scandinavian Simvastatin Survival Study (4S)," *Lancet*, 1994, 344:1383–1389.

Tomoda et al., "Ferroverdins, Inhibitors of Cholesteryl Ester Transfer Protein Produced by *Streptomyces* sp. WK–5344," *J. Antibiotics*, 1999, 52(12):1101–1107.

Trammell, "The Total Synthesis of (±)–Puupehenone," *Tetrahedron Letters*, 1978, 18:1525–1528.

Ungur et al., "Absolute sterochemistry of natural sesquiterpenoid diacylglycerols," *Tetrahedron: Asymmetry*, 1999, 10:1263–1273.

Urban and Capon, "Absolute Stereochemistry of Puupehenone and Related Metabolities," *J. Nat. Prod.*, 1996, 59:900–901.

Vedejs et al., "Transition–Metal Peroxide Reactions. Synthesis of α–Hydroxycarbonyl Compounds from Enolates," *J. Org. Chem.*, 1978, 43(2):188–196.

COMPOUNDS AFFECTING CHOLESTEROL ABSORPTION

STATEMENT AS TO FEDERALLY SPONSORED RESEARCH

Funding for the work described above herein was provided in part by the federal government, which may have certain rights in the invention. This application was supported by government funding from the following agencies: NASA under grant number NCC8-131, National Institute of Health under grant number CA86842, and National Science Foundation under grant number 0078921.

TECHNICAL FIELD

This invention relates to novel organic compound and methods for their synthesis. More particularly, the invention relates to novel compounds affecting lymphatic absorption of cholesterol.

BACKGROUND

Atherosclerosis is a major cause of heart attack, stroke, and gangrene of the extremities and can be attributed directly to having high levels of cholesterol in the body. Cholesterol can enter the body by absorption from foods by the intestinal mucosal cells and the lymphatic system (i.e., exogenous sources). Cholesterol also is produced in the liver by a sequence of enzymatic reactions (i.e., endogenous biosynthesis). Endogenous biosynthesis of cholesterol involves a key enzyme, HMG-CoA (3-hydroxy-3-methylglutaryl coenzyme A) reductase. HMG-CoA reductase inhibitors can be used to lower total plasma cholesterol in patients with primary hypercholesterolemia. Effective inhibition of HMG-CoA reductase is realized by drugs such as Lovastatin (sold as Mevacor from Merck Co.), Mevalotin (from Sankyo Co., Japan), and analogs thereof (e.g., compounds sold under the trade names Sivastatin, Mevastatin, and Pravastatin). Exogenous sources of cholesterol, however, are not affected by these drugs. Various compounds have been reported to be useful for lowering cholesterol absorption. See, e.g., U.S. Pat. Nos. 5,246,960, 5,175,186, 5,215, 972, 5,495,048, 5,856,503, and 5,637,771. Currently, a lipase inhibitor termed Xenical® has been offered for obesity management. Xenical® has been reported to achieve a slight reduction in cholesterol.

SUMMARY

The invention features a compound of Formula I:

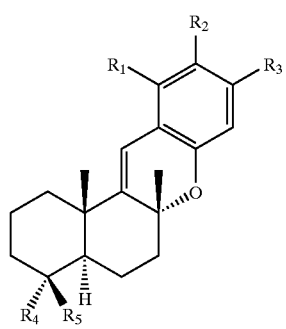

(I)

$R_1$ can be independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, or alkylsilyloxy.

$R_2$ can be independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, or phenylselenyl, thiol, arylsulfenyl, alkylsulfenyl, arylsulfinyl, or alkylsilyloxy;

$R_3$ can be independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, or alkylsilyloxy.

$R_4$ can be independently hydrido, alkyl, or hydroxyalkyl.

$R_5$ can be independently hydrido, alkyl, or hydroxyalkyl.

In some embodiments, $R_1$ is halo, $R_2$ and $R_3$ are hydroxy, and $R_4$ and $R_5$ are alkyl in the compound, e.g., $R_1$ is chloro and $R_4$ and $R_5$ are methyl. In other embodiments, $R_1$ is halo, $R_2$ and $R_3$ are alkylsilyloxy, and $R_4$ and $R_5$ are alkyl, e.g., $R_1$ is chloro, $R_2$ and $R_3$ are OSi-t-BuMe2, and $R_4$ and $R_5$ are methyl. In one embodiment, the compound has Formula (24):

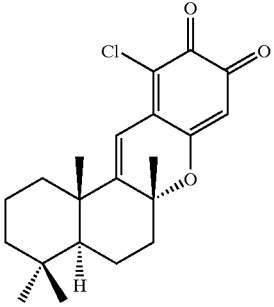

(24)

The invention also features a compound of Formula II:

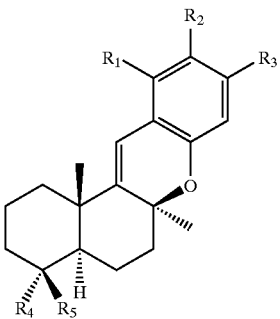

(II)

$R_1$ can be independently any of the groups described above for $R_1$ of Formula I. $R_2$ can be independently any of the groups described above for $R_2$ of Formula I. $R_3$ can be independently any of the groups described above for $R_3$ of Formula I. $R_4$ can be independently hydrido, alkyl, or hydroxyalkyl. $R_5$ can be independently hydrido, alkyl, or hydroxyalkyl. However, when $R_1$ is chloro, $R_2$ and $R_3$ are not hydroxy and $R_4$ and $R_5$ are methyl.

In some embodiments, $R_1$ is halo, $R_2$ and $R_3$ are hydroxy, and $R_4$ and $R_5$ are alkyl. In some embodiments, $R_1$ is halo, $R_2$ and $R_3$ are alkylsilyloxy; and $R_4$ and $R_5$ are alkyl, e.g., $R_1$ is chloro, $R_2$ and $R_3$ are OSi-t-BuMe$_2$, and $R_4$ and $R_5$ are methyl.

The invention also features a compound of Formula III:

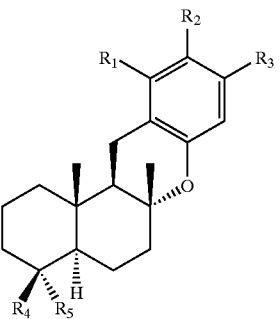

(III)

In these compounds, $R_1$ can be independently any of the groups described above for R1 of Formula I.

$R_2$ can be independently any of the groups described above for $R_2$ of Formula I. $R_3$ can be independently any of the groups described above for $R_3$ of Formula I. $R_4$ can be independently hydrido, alkyl, or hydroxyalkyl. $R_5$ can be independently hydrido, alkyl, or hydroxyalkyl.

In some embodiments, $R_1$ is halo, $R_2$ and $R_3$ are selected from hydroxy and alkylsilyloxy, and $R_4$ and $R_5$ are alkyl, e.g., $R_1$ is chloro, $R_2$ and $R_3$ are hydroxy, and $R_4$ and $R_5$ are methyl. In some embodiments, $R_1$ is halo, $R_2$ and $R_3$ are alkylsilyloxy, and $R_4$ and $R_5$ are methyl, e.g., $R_1$ is chloro, $R_2$ and $R_3$ are OSi-t-BuMe$_2$, and $R_4$ and $R_5$ are methyl. In some embodiments the compound has Formula (23):

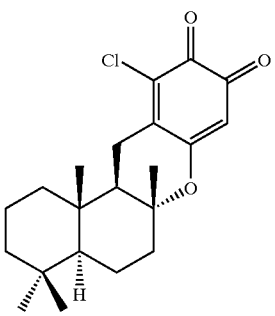

(23)

The invention also features a compound of Formula IV:

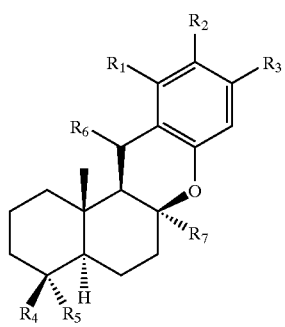

(IV)

$R_1$ can be independently any of the groups described above for $R_1$ of Formula I. $R_2$ can be independently any of the groups described above for $R_2$ of Formula I. $R_3$ can be independently any of the groups described above for $R_3$ of Formula I. $R_4$ can be independently hydrido, alkyl, or hydroxyalkyl. $R_5$ can be independently hydrido, alkyl, or hydroxyalkyl. $R_6$ can be independently hydrido, hydroxy, or acyloxy. $R_7$ can be independently alkyl, or arylselenylalkyl.

In some embodiments, $R_1$ is halo, $R_2$ and $R_3$ are selected from hydroxy, alkylsilyloxy, or aralkyloxy, $R_4$ and $R_5$ are alkyl, $R_6$ is selected from hydrido, hydroxy, or acyloxy, and $R_7$ is selected from alkyl or arylselenylalkyl, e.g., $R_1$ is chloro; $R_2$ and $R_3$ are OSi-t-BuMe$_2$, $R_4$ and $R_5$ are methyl, $R_6$ is hydrido, and $R_7$ is methyl. In other embodiments, $R_1$ is chloro, $R_2$ and $R_3$ are hydroxy, $R_4$ and $R_5$ are methyl, $R_6$ is hydrido, and $R_7$ is methyl. In some embodiments, $R_1$ is chloro; $R_2$ and $R_3$ are arylalkyloxy; $R_4$ and $R_5$ are methyl, $R_6$ is hydroxy, and $R_7$ is arylselenylalkyl. In some embodiments, $R_1$ is chloro,; $R_2$ and $R_3$ are arylalkyloxy, and $R_4$ and $R_5$ are methyl, $R_6$ is acyloxy, and $R_7$ is arylselenylalkyl. In some embodiments, $R_1$ is chloro, $R_2$ and $R_3$ are arylalkyloxy; $R_4$ and $R_5$ are methyl, $R_6$ is acyloxy, and $R_7$ is methyl.

The invention also features a compound of Formula V:

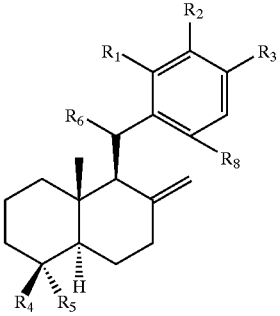

(V)

R₁ can be independently any of the groups described above for R₁ of Formula I. R₂ can be independently any of the groups described above for R₂ of Formula I. R₃ can be independently any of the groups described above for R₃ of Formula I. R₄ can be independently hydrido, alkyl, or hydroxyalkyl. R₅ is independently hydrido, alkyl, or hydroxyalkyl. R₆ can be hydroxy. R₈ can be independently hydroxy, or alkylsilyloxy.

In some embodiments, R₁ is halo; R₂ and R₃ are arylalkyloxy; R₄ and R₅ are alkyl; R₆ is hydroxy; and R₈ is selected from hydroxy and alkylsilyloxy, e.g., R₁ is chloro; R₂ and R₃ are OBn; and R₄ and R₅ are methyl; R₆ is hydroxy; and R₈ is OSi-tBuMe₂. In some embodiments, R₁ is chloro; R₂ and R₃ are OBn; R₄ and R₅ are methyl; R₆ is hydroxy; and R₈ is hydroxy.

The inventions also features a method of synthesizing a compound of Formula I:

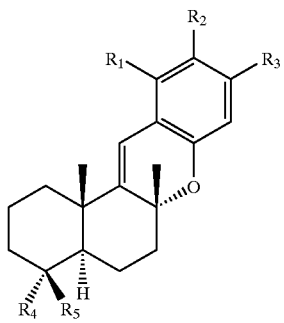

(I)

wherein R₁ is chloro, R₂ and R₃ are hydroxy, and R₄ and R₅ are methyl. The method comprises reacting compound (4) with compound (3) to form intermediate compound (18).

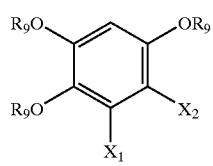

(4)

wherein R₉ is OSi-t-BuMe₂, X₁ is chloro, X₂ is bromo;

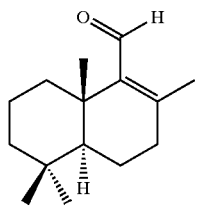

(3)

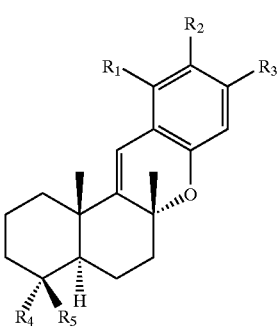

(18)

wherein R₁ is chloro, R₂ and R₃ are OSi-tBuMe₂. The method further comprises isolating compound (18) and deprotecting compound (18). The result is a compound of Formula I.

The invention also features a method of synthesizing (+) chloropuupehenone. The method comprises hydrogenating compound (19) to form compound (25).

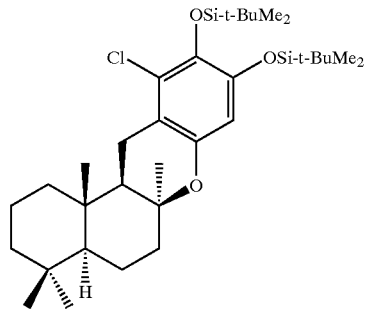

(25)

Desilylation of compound (25) forms compound (26).

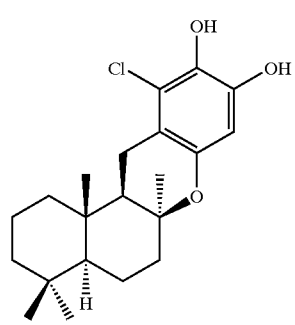

(26)

Oxidation of compound (26) forms (+) chloropuupehenone (27).

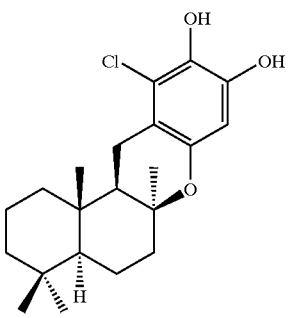
(27)

The invention also features a pharmaceutical composition comprising a pharmaceutically-acceptable carrier and a compound of Formula 1:

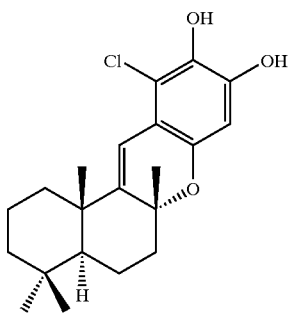
(1).

The composition can be in the form of a capsule or a liquid emulsion. The composition can in a controlled release formulation, e.g., a dispersion in hydroxypropylmethyl cellulose, or in a formulation suitable for parenteral administration, e.g., a lipid emulsion. The composition can comprise a diluent such as polyethylene glycol, propylene glycol, ethanol, corn oil, cottonseed oil, peanut oil, sesame oil, or benzyl alcohol. The pharmaceutically-acceptable carrier material can be lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, microcrystalline cellulose, sodium starch glycolate, sodium lauryl sulfate, povidone, polyvinylpyrrolidone, or polyvinyl alcohol.

The invention also features a method for identifying a compound that inhibits lymphatic absorption of cholesterol. The method comprises administering a known amount of cholesterol and a compound of claim 1 to a non-human mammal, and determining the amount of administered cholesterol that is absorbed by the lymph. A statistically significant decrease in lymphatic cholesterol absorption relative to the lymphatic cholesterol absorption of a corresponding control mammal indicates that the compound is effective for inhibiting lymphatic absorption of cholesterol. A statistically insignificant change or a statistically significant increase in lymphatic cholesterol absorption relative to the lymphatic cholesterol absorption of a corresponding control mammal indicates the compound does not inhibit lymphatic absorption of cholesterol. The cholesterol and the compound can be administered in a lipid emulsion.

The invention also features a method of treating a cholesterol-related condition. The method comprises administering an effective amount of a compound of Formula I to a mammal. The cholesterol-related condition can be, for example, atherosclerosis, hypercholesterolemia, heart attack, gangrene, and stroke. The compound can be administered orally, intravascularly, intraperitoneally, subcutaneously, intramuscularly, or topically, and in an amount from about 4 mg/kg to about 4 g/kg of body weight per day. The compound can be administered in a composition as described above. The method can be part of a treatment regimen comprising a diet low in cholesterol, or as part of a treatment regimen that includes administering an HMG-CoA reductase inhibitors. The method can be used to treat humans. The method can include administering the compound for 7 days or more, e.g., for one year or more.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Compounds of Formula I

Figure 1:
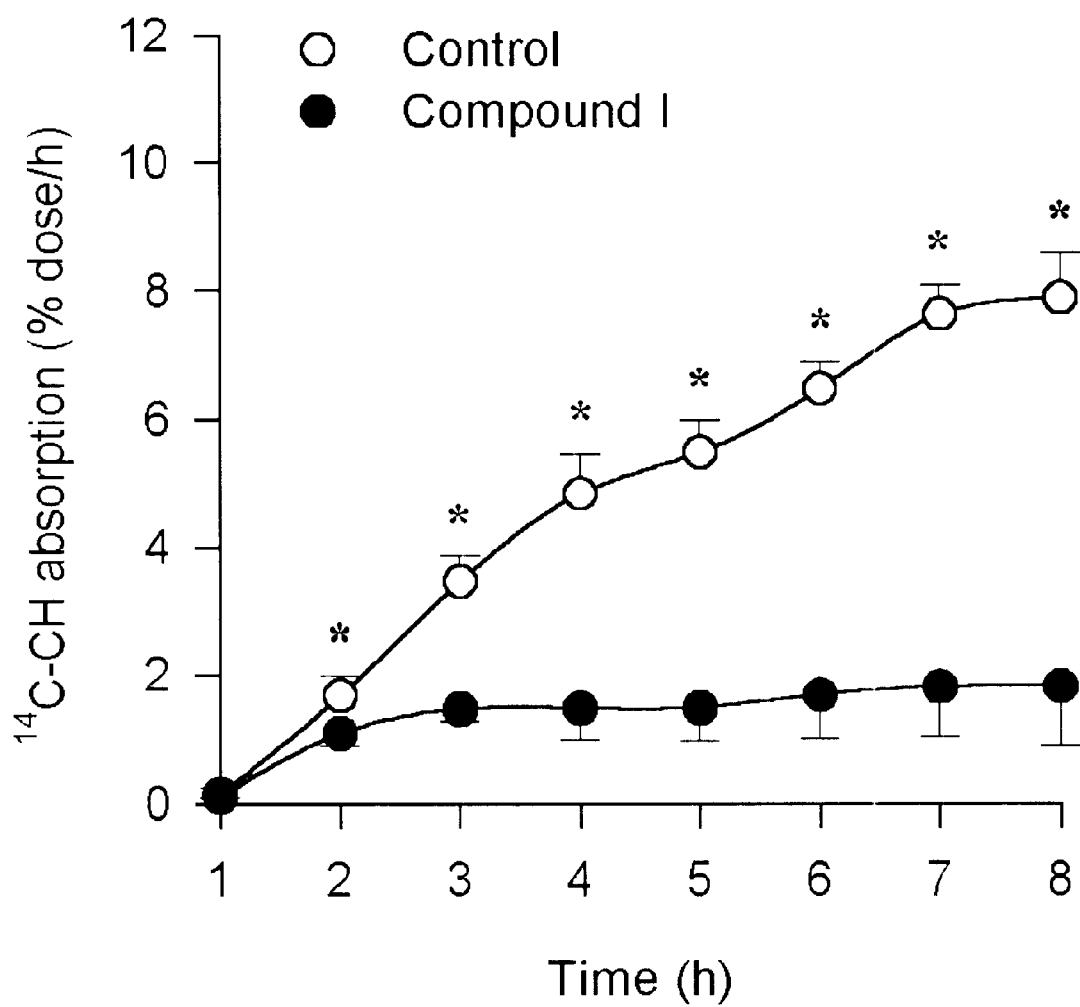
FIG. 1 is a graph showing hourly rates of lymphatic absorption of cholesterol in lymph-cannulated rats. Values are expressed as means±SD, n=5. *Indicates a significant difference between treatments at p<0.05.

A class of compounds useful for inhibiting lymphatic absorption of cholesterol is defined by Formula I:

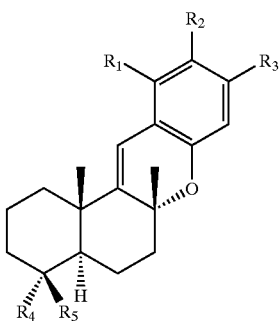
(I)

wherein $R_1$ is selected from hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, and alkylsilyloxy.

$R_2$ is selected from hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, and alkylsilyloxy.

$R_3$ is selected from hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, and alkylsilyloxy.

$R_4$ is selected from hydrido, alkyl, and hydroxyalkyl, and $R_5$ is selected from hydrido, alkyl, and hydroxyalkyl. The class of compounds also includes pharmaceutically-acceptable salts thereof.

An exemplary class of compounds includes compounds of Formula I, wherein $R_1$ is halo, $R_2$ is selected from hydroxy and alkylsilyloxy, $R_3$ is selected from hydroxy and alkylsilyloxy, $R_4$ is selected from hydrido, alkyl and hydroxyalkyl; and $R_5$ is selected from hydrido, alkyl and hydroxyalkyl.

A family of specific compounds of particular interest within Formula I includes compounds and their pharmaceutically acceptable salts thereof as follows:

(4aS,6aR,12bS)-2H-11-Chloro-1,3,4,4a,5,6,6a,12b-octahydro-4,4,6a,12b-tetramethyl-benzo[a]xanthene-9,10-diol (1); and (4aS,6aR,12bS)-2H-9,10-Bis-(t-butyldimethylsilyloxy)-11-chloro-1,3,4,4a,5,6,6a,12b-octahydro-4,4,6a,12b-tetramethyl-benzo[a]xanthene (18).

Compounds of Formula II

A second class of compounds is defined by Formula II:

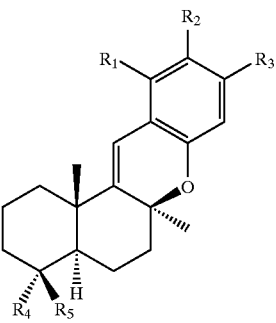

(II)

wherein $R_1$ is selected from moieties described above for $R_1$ groups of Formula I, $R_2$ is selected from the moieties described above for $R_2$ groups of Formula I, $R_3$ is selected from the moieties described above for $R_3$ groups of Formula I, $R_4$ is selected from hydrido, alkyl, and hydroxyalkyl, and $R_5$ is selected from hydrido, alkyl, and hydroxyalkyl. The class of compounds also includes pharmaceutically-acceptable salts thereof.

An exemplary class of compounds includes those compounds of Formula II wherein $R_1$ is halo, $R_2$ is selected from hydroxy and alkylsilyloxy; $R_3$ is selected from hydroxy, and alkylsilyloxy; $R_4$ is selected from hydrido, alkyl and hydroxyalkyl; and $R_5$ is selected from hydrido, alkyl and hydroxyalkyl.

A family of specific compounds of particular interest within Formula II consists of compounds and their pharmaceutically acceptable salts as follows:

(4aS,6aS,12bS)-2H-9,10-Bis-(t-butyldimethylsilyloxy)-11-chloro-1,3,4,4a,5,6,6a,12b-octahydro-4,4,6a,12b-tetramethyl-benzo[a]xanthene (19).

Compounds of Formula III

A third class of compounds is defined by Formula III:

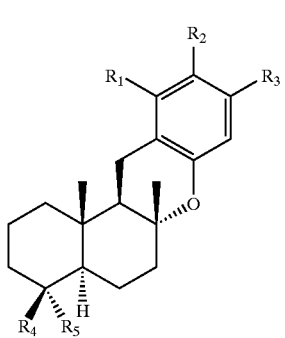

(III)

wherein $R_1$ is selected from the moieties described above for $R_1$ groups of Formula I, $R_2$ is selected from the moieties described above for $R_2$ groups of Formula I, $R_3$ is selected from the moieties described above for $R_3$ groups of Formula I, $R_4$ is selected from hydrido, alkyl and hydroxyalkyl, and $R_5$ is selected from hydrido, alkyl and hydroxyalkyl. The class of compounds also includes pharmaceutically-acceptable salts thereof.

An exemplary class of compounds includes those compounds of Formula III wherein $R_1$ is halo, $R_2$ is selected from hydroxy and alkylsilyloxy; $R_3$ is selected from hydroxy and alkylsilyloxy; $R_4$ is selected from hydrido, alkyl and hydroxyalkyl; and $R_5$ is selected from hydrido, alkyl, and hydroxyalkyl.

A family of specific compounds of particular interest within Formula III includes compounds and their pharmaceutically acceptable salts as follows:

(4aS,6aR,12aR,12bS)-2H-9,10-Bis-(t-butyldimethylsilyloxy)-11-chloro-1,3,4,4a,5,6,6a,12,12a,12b-decahydro-4,4,6a,12b-tetramethyl-benzo[a]xanthene (21); and (4aS,6aR,12aR,12bS)-2H-11-Chloro-1,3,4,4a,5,6,6a,12,12a,12b-decahydro-4,4,6a,12b-tetramethyl-benzo[a]xanthene-9,10-diol (22).

A second family of specific compounds of particular interest within Formula III includes oxidation products and their pharmaceutically acceptable salts as follows:

(4aS,6aR,12aR,12bS)-2H-11-Chloro-1,3,4,4a,5,6,6a,9,10,12,12a,12b-dodecahydro-4,4,6a,12b-tetramethyl-benzo[a]xanthene-9,10-dione (23); and (4aS,6aR,12aR,12bS)-2H-11-Chloro-1,3,4,4a,5,6,6a,12,12a,12b-decahydro-4,4,6a,12b-tetramethyl-benzo[a]xanthene-9,10-diol (22).

Compounds of Formula IV

A fourth class of compounds is defined by Formula IV:

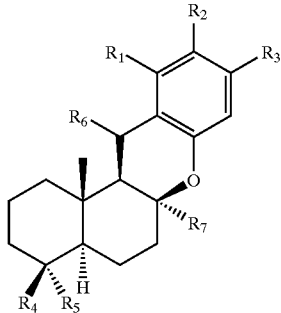

(IV)

wherein $R_1$ is selected from the moieties described above for $R_1$ groups of Formula I, $R_2$ is selected from the moieties described above for $R_2$ groups of Formula I, $R_3$ is selected from the moieties described above for $R_3$ groups of Formula I, $R_4$ is selected from hydrido, alkyl, and hydroxyalkyl, $R_5$ is selected from hydrido, alkyl, and hydroxyalkyl, $R_6$ is selected from hydrido, hydroxy, and acyloxy, and $R_7$ is selected from alkyl and arylselenylalkyl. The class of compounds also includes pharmaceutically-acceptable salts thereof.

An exemplary class of compounds includes those compounds of Formula IV wherein $R_1$ is halo, $R_2$ is selected from hydroxy, alkylsilyloxy, and aralkyloxy; $R_3$ is selected from hydroxy, alkylsilyloxy, and aralkyloxy; $R_4$ is selected from hydrido, alkyl, and hydroxyalkyl; $R_5$ is selected from hydrido, alkyl, and hydroxyalkyl; $R_6$ is selected from hydrido, hydroxy, and acyloxy; and $R_7$ is selected from alkyl and arylselenylalkyl.

A family of specific compounds of particular interest within Formula IV includes the following compounds and their pharmaceutically acceptable salts as follows:

(4aS,6aS,12aR,12bS)-2H-9,10-Bis-(t-butyldimethylsilyloxy)-11-chloro-1,3,4,4a,5,6,6a,12,12a,12b-decahydro-4,4,6a,12b-tetramethyl-benzo[a]xanthene (25); (4aS,6aS,12aR,12bS)-2H-11-Chloro-1,3,4,4a,5,6,6a,12,12a,12b-decahydro-4,4,6a,12b-tetramethyl-benzo[a]xanthene-9,10-diol (26); (4aS,6aR,12aS,12bS)-2H-9,10-Bis-benzyloxy)-11-chloro-hydroxy-6a-(phenylselenylmethyl)-1,3,4,4a,5,6,6a,12,12a,12b-decahydro-4,4,12b-trimethyl-benzo[a]xanthene (40); (4aS,6aR,12aS,12bS)-2H-12-Acetoxy-9,10-bis-(benzyloxy)-11-chloro-6a-(phenylselenylmethyl)-1,3,4,4a,5,6,6a,12,12a,12b-decahydro-4,4,12b-trimethyl-benzo[a]xanthene (41); and (4aS,6aS,12aS,12bS)-2H-12-Acetoxy-9,10-bis-(benzyloxy)-11-chloro-1,3,4,4a,5,6,6a,12,12a,12b-decahydro-4,4,6a,12b-tetramethyl-benzo[a]xanthene (42).

Compounds of Formula V

A fifth class of compounds is defined by Formula V:

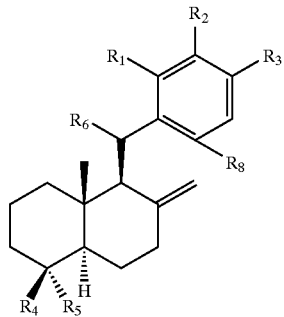

(V)

wherein $R_1$ is selected from the moieties described above for $R_1$ groups of Formula I, $R_2$ is selected from the moieties described above for $R_2$ groups of Formula I, $R_3$ is selected from the moieties described above for $R_3$ groups of Formula I, $R_4$ is selected from hydrido, alkyl, and hydroxyalkyl, $R_5$ is selected from hydrido, alkyl, and hydroxyalkyl, $R_6$ is hydroxy, and $R_8$ is selected from hydroxy and alkylsilyloxy. The class of compounds also includes pharmaceutically-acceptable salts thereof.

An exemplary class of compounds includes those compounds of Formula V wherein $R_1$ is halo; $R_2$ is selected from hydroxy, alkylsilyloxy and aralkyloxy; $R_3$ is selected from hydroxy, alkylsilyloxy, and aralkyloxy; $R_4$ is selected from hydrido, alkyl, and hydroxyalkyl; $R_5$ is selected from hydrido, alkyl, and hydroxyalkyl; $R_6$ is hydroxy; and $R_8$ is selected from hydroxy and alkylsilyloxy.

A family of specific compounds of particular interest within Formula V includes the following compounds and their pharmaceutically acceptable salts as follows: (4aS,8aS)-1-{[2-chloro-3,4-dibenzyloxy-6-(t-butyldimethylsilyloxy)]phenylhydroxymethyl}-2-methylene-5,5,8a-trimethyldecahydronaphthalene (37); and (4aS,8aS)-1-{[2-chloro-3,4-dibenzyloxy-6-hydroxy] phenylhydroxymethyl]-2-methylene-5,5,8a-trimethyldecahydronaphthalene (38).

The term "alkyl" embraces linear or branched saturated aliphatic radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about four carbon atoms. Examples of such radicals include methyl, ethyl, n-propyl, isopropyl, n-butyl, isobutyl, sec-butyl, tert-butyl, pentyl, iso-amyl, hexyl, octyl and the like. The term alkyl also includes cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups.

The term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "arylalkyl" moiety is an alkyl substituted with an aryl (e.g., phenylmethyl (benzyl)). The term "n-alkyl" means a straight chain (i.e. unbranched) unsubstituted alkyl group.

The term "alkenyl" includes unsaturated aliphatic groups analogous in length and possible substitution to the alkyls described above, but that contain at least one double bond and must contain at least two carbon atoms. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups.

The term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro chloro or bromo to provide "haloalkoxy" or "haloalkoxyalkyl" radicals. Examples of "alkoxy" radicals include methoxy butoxy and trifluoromethoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" embraces unsaturated heterocyclic radicals. Examples of unsaturated heterocyclic radicals, also termed "heteroaryl" radicals include thienyl, pyrryl, furyl, pyridyl, pyrimidyl, pyrazinyl, pyrazolyl, oxazolyl, isoxazolyl, imidazolyl, thiazolyl, pyranyl and tetrazolyl. The term also embraces radicals where heterocyclic radicals are fused with aryl radicals. Examples of such fused bicyclic radicals include benzofuran, benzothiophene, and the like. The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl" or "sulfonamidyl", whether alone or used with terms such as "N-alkylsulfamyl", "N-arylsulfamyl", "N,N-dialkylsulfamyl" and "N-alkyl-N-arylsulfamyl", denotes a sulfonyl radical substituted with an amine radical, forming a sulfonamide (—$SO_2NH_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted, respectively, with one aryl radical, and one alkyl and one aryl radical. The terms "carboxy" or "carboxyl", whether used alone or with other terms, such as "carboxyalkyl", denotes —$CO_2H$. The term "carboxyalkyl" embraces radicals having a carboxy radical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. An example of an "alkylcarbonyl" radical is $CH_3$—(C=O)—. The term "alkylcarbonylalkyl", denotes an alkyl radical substituted with an "alkylcarbonyl" radical. The term "alkoxycarbonyl" means a radical containing an alkoxy radical, as defined above, attached via an oxygen atom to a carbonyl (C=O) radical. Examples of such "alkoxycarbonyl" radicals include $(CH_3)_3CO—C(=O)—$ and $—(O=)C—OCH_3$. The term "alkoxycarbonylalkyl" embraces radicals having "alkoxycarbonyl", as defined above substituted to an alkyl radical. Examples of such "alkoxycarbonylalkyl" radicals include $(CH_3)_3COC(=O)(CH_2)_2—$ and $—(CH_2)_2(=O)COCH_3$. The term "amido" when used by itself or with other terms such as "amidoalkyl", "N-monoalkylamido", "N-monoarylamido", "N,N-dialkylamido", "N-alkyl-N-arylamido", "N-alkyl-N-hydroxyamido" and "N-alkyl-N-hydroxyamidoalkyl", embraces a carbonyl radical substituted with an amino radical. The terms "N-alkylamido" and "N,N-dialkylamido" denote amido groups which have been substituted with one alkyl radical and with two alkyl radicals, respectively. The terms "N-monoarylamido" and "N-alkyl-N-arylamido" denote amido radicals substituted, respectively, with one aryl radical, and one alkyl and one aryl radical. The term "N-alkyl-N-hydroxyamido" embraces amido radicals substituted with a hydroxyl radical and with an alkyl radical. The term "N-alkyl-N-hydroxyamidoalkyl" embraces alkyl radicals substituted with an N-alkyl-N-hydroxyamido radical. The term "amidoalkyl" embraces alkyl radicals substituted with amido radicals. The term "aminoalkyl" embraces alkyl radicals substituted with amine radicals. The term "alkylaminoalkyl" embraces aminoalkyl radicals having the nitrogen atom substituted with an alkyl radical. The term "amidino" denotes an $—C(=NH)—NH_2$ radical. The term "cyanoamidino" denotes an $—C(=N—CN)—NH_2$ radical. The term "heterocycloalkyl" embraces heterocyclic-substituted alkyl radicals such as pyridylmethyl and thienylmethyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl and cycloheptyl. The term "cycloalkenyl" embraces unsaturated radicals having three to ten carbon atoms, such as cylopropenyl, cyclobutenyl cyclopentenyl cyclohexenyl and cycloheptenyl. The term "alkylthio" embraces radicals containing a linear or branched alkyl radical, of one to ten carbon atoms, attached to a divalent sulfur atom. The term "arylsulfenyl" embraces aryl radicals attached to a divalent sulfur atom (—SAr) An example of "alkylthio" is methylthio, $(CH_3—S—)$. The term "alkylsulfinyl" embraces radicals containing a linear or branched alkyl radical, of one to ten carbon atoms, attached to a divalent —S(=O)— atom. The term "arylsulfinyl" embraces aryl radicals attached to a divalent —S(=O)— atom (e.g., —S=OAr). The terms "N-alkylamino" and "N,N-dialkylamino" denote amine groups which have been substituted with one alkyl radical and with two alkyl radicals, respectively. The term "acyl", whether used alone, or within a term such as "acylamino", denotes a radical provided by the residue after removal of hydroxyl from an organic acid. The term "acylamino" embraces an amine radical substituted with an acyl group. An examples of an "acylamino" radical is acetylamine $(CH_3C(=O)—NH—)$. The term "aryloxy" denotes a radical provided by the residue after removal of hydrido from a hydroxy-substituted aryl moiety (e.g., phenol). The term "alkylsilyl" denotes a silyl radical substituted with an alkyl group. The term "alkylsilyloxy" denotes a silyloxy radical (—O—Si—) substituted with an alkyl group. An example of an "alkylsilyloxy" radical is $—O—Si-t-BuMe_2$. The term "arylselenylalkyl" denotes an alkyl radical substitute with a selenylaryl group. An example of an "arylselenylalkyl" radical is $—CH_2SePh$.

Also included in the family of compounds of Formulae I-V are pharmaceutically-acceptable salts thereof. The term "pharmaceutically-acceptable salts" embraces salts commonly used to form alkali metal salts and to form addition salts of free acids or free bases. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I, II, III, IV, or V by reacting, for example, the appropriate acid or base with the compound of Formula I, II, III, IV, or V.

Pharmaceutical Compositions

The present invention includes a pharmaceutical composition for inhibiting lymphatic absorption of cholesterol, comprising a therapeutically-effective amount of a compound of Formula I in association with at least one pharmaceutically-acceptable carrier, adjuvant or diluent.

A pharmaceutical composition comprises one or more compounds of Formulae I-V in association with one or more non-toxic, pharmaceutically acceptable carriers and/or diluents and/or adjuvants (collectively referred to herein as "carrier" materials) and, if desired, other active ingredients. A compound of the present invention may be administered by any suitable route, preferably in the form of a pharmaceutical composition adapted to such a route, and in a dose effective for the treatment intended. A compound may, for example, be administered orally, intravascularly, intraperitoneally, subcutaneously, intramuscularly or topically.

For oral administration, a pharmaceutical composition may be in the form of, for example, a tablet, capsule, emulsion, suspension or solution. A pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely.

If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, microcrystalline cellulose, sodium starch glycolate, sodium lauryl sulfate, povidone, polyvinylpyrrolidone, and/or polyvinyl alcohol, and then tableted or encapsulated for convenient administration. Capsule or tablet shells can contain, e.g., gelatin, titanium dioxide, and dyes. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Methods

Compounds of Formula I and related compounds can be utilized in the treatment of cholesterol-related conditions in mammals, including humans, dogs and cats. Cholesterol-related conditions include, for example, atherosclerosis, hypercholesterolemia, heart attack, stroke, and gangrene of the extremities. A method of treatment includes administering an effective amount of a compound of Formula I. The compound can be administered as a pharmaceutical composition, as described above. A compound of the present invention may be administered by any suitable route, typically in the form of a pharmaceutical composition adapted to such a route, and in a dose effective for the treatment intended. A compound may, for example, be administered orally, intravascularly, intraperitoneally, subcutaneously, intramuscularly or topically.

The amount of compound that is administered and the dosage regimen for treating a disease condition with the compounds and/or compositions of this invention depends on a variety of factors and can be determined by an attending physician. These factors include the age, body weight, sex and medical condition of the subject, the severity of the disease, the route and frequency of administration, the particular compound employed, health status, diet, other medications, and other relevant clinical factors. The amount of compound administered can range from about 4 mg/kg body weight per day to about 4 g/kg of body weight per day. For example, a compound can be administered at a daily dosage of 5 mg/kg, 10 mg/kg, 100 mg/kg, 250 mg/kg, 1000 mg/kg, 1500 mg/kg, 2000 mg/kg, or 3000 mg/kg. The daily dosage can be administered once per day, twice per day, three times per day, or four or more times per day. Variations in these dosage levels can be adjusted using standard empirical routines for optimization.

The concentration of a compound of the present invention effective to treat a cholesterol-related condition in a mammal may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the overall health status of the particular patient and the relative biological efficacy of the compound selected. The amount and dosage regimen effective for treating a cholesterol-related condition in a mammal can be determined by, e.g., measuring cholesterol levels prior to the start of treatment and at various times after treatment has commenced. Assays for the quantitation of cholesterol are known, including assays for the level of cholesterol in blood or in lymph. Administration of an effective amount results in a decrease in lymphatic absorption of cholesterol that is statistically significant at a $p \leq 0.05$ with an appropriate parametric or non-parametric statistic, e.g., Chi-square test, Student's t-test, Mann-Whitney test, or F-test. In some embodiments, a difference in cholesterol level is statistically significant at $p<0.01$, $p<0.005$, or $p<0.001$.

A compound of the present invention can be administered as a single dose or can be administered for a period of from one day to many years, e.g., for 3 days or more, for 7 days or more, for 14 days or more, for 30 days or more, for one year or more, or for 3 years or more. The duration of the administration period depends upon, e.g., the daily dosage, the type of cholesterol-related condition and the patient's response to the compound.

A compound of the present invention can be administered in conjunction with a diet low in cholesterol as part of a cholesterol lowering treatment regime. A compound of the present invention also can be administered in conjunction with drugs such as Lovastatin (sold as Mevacor from Merck Co.), Mevalotin (from Sankyo Co., Japan), and analogs thereof (e.g., compounds sold under the trade names Sivastatin, Mevastatin, and Pravastatin), to lower total cholesterol levels and to prevent and treat cholesterol-related conditions, e.g., hypercholesterolemia. A compound of the invention also can be administered in conjunction with Xenical®, a prescription medication offered for use in weight loss regimens.

Compounds of Formulae I-V also can be tested for their effect on lymphatic absorption of dietary cholesterol. Methods for measuring lymphatic absorption of cholesterol in vivo are known. A suitable in vivo method is described in Loest, et al., J. Nutr. 132: 1282–1288 (2002).

Typically, a method of measuring inhibition of cholesterol absorption in vivo involves administering a predetermined amount of cholesterol and a test compound of Formulae I-V to the intestine of a mammal. Typically, the animal is a fasted mammal. The cholesterol and test compound can be administered in a lipid emulsion into the duodenum of the mammal over a period of a few hours. Suitable non-human mammals include rats, mice, guinea pigs, and hamsters. The amount of administered cholesterol that appears in the mesenteric lymph of the mammal is determined at various times during and after administration, typically at hourly intervals. The amount of cholesterol present in the lymph is compared to the amount present in a control animal that has had cholesterol but no test compound administered. If the amount of cholesterol appearing in the lymph of the test animal is statistically significantly less than the amount of cholesterol in the lymph of the control animal, it is concluded that the compound can inhibit intestinal absorption of cholesterol.

General Synthetic Procedures

The compounds of the invention can be synthesized according to the procedures of Schemes 1–6, wherein the $R_1$–$R_8$ substituents are as defined for Formulae I-V, above, except where further noted.

Scheme 1 shows the synthesis of enantiopure A-B fragment 3 from commercially available 3aR-(+)-sclareolide 5 (purchased from Aldrich Chemical Company). Deprotonation of optically pure lactone 5 with LDA (lithium diisopropylamide) in THF at −78° C., followed by treatment with MoO$_5$·pyridine·HMPA[13] complex gave two diasteromers, 6 (65.6% yield) and 7 (12.4% yield)) (which were separated by silica gel chromatography), along with 20% recovery of starting sclareolide 5. Treatment of a mixture of 6 and 7 with lithium aluminum hydride in THF at room temperature gave triol 8 (70% yield) and lactol 9 (30% yield). Oxidative cleavage of 8 with lead tetraacetate in benzene at 25° C. provided an 90% yield of 10, and oxidative cleavage of 9 under similar conditions gave an 85% yield of 11. Dehydration of alcohol 10 with p-toluenesulfonic acid in refluxing toluene for 2 h gave a 78% yield of enal 3. Basic hydrolysis of the formyl ester group of 11 with potassium carbonate in methanol at 0° C. provided a 92% yield of 10, which was converted into 3, as described above. The preparation of compound 3 from (−)-sclareol using a different synthetic method has been reported previously (Reeves, P. G. (1996)).

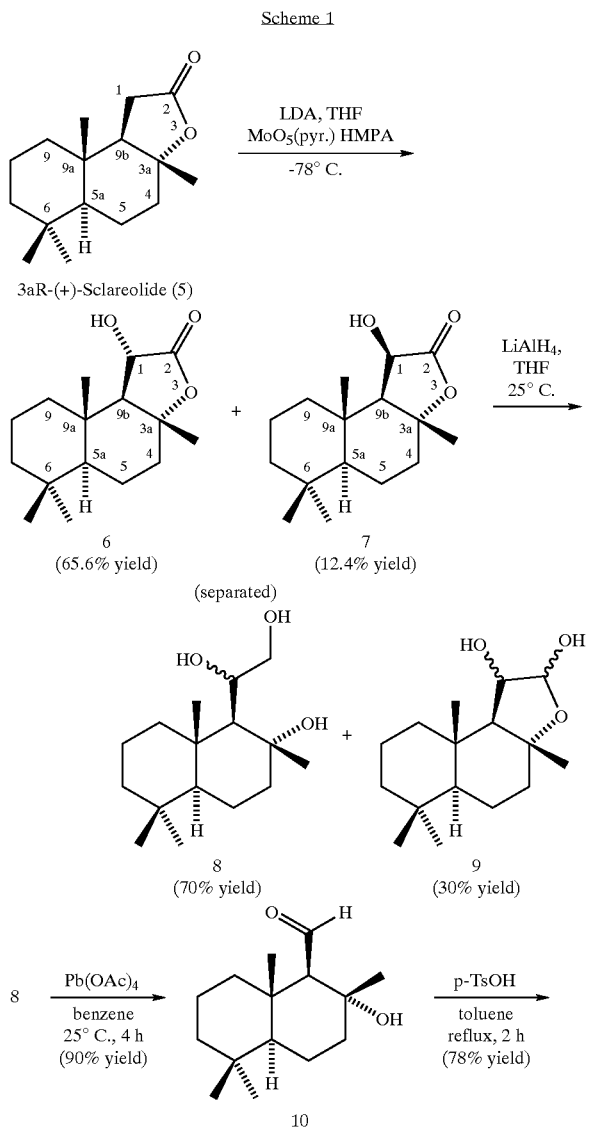

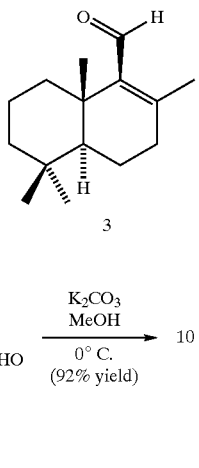

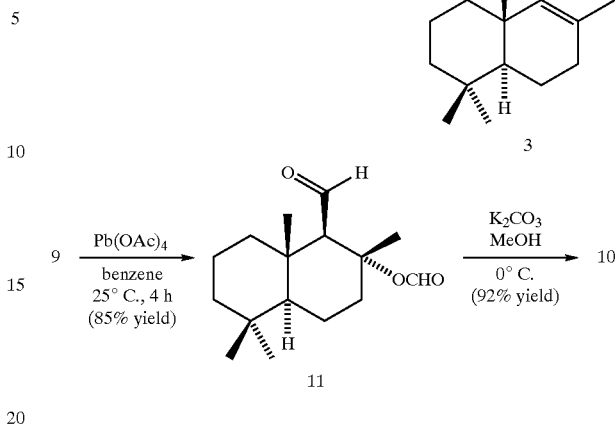

Scheme 2 shows the preparation of D-ring fragment 4 starting from 3-chlorovanillin 12, derived from the chlorination of vanillin with chlorine in acetic acid (85% yield), according to the procedure of Hann et al. (J. Am. Chem. Soc., 1927, 49, 535–7). Demethylation of 12 with BBr$_3$ in CH$_2$Cl$_2$ (94% yield) followed by protection of the diol with t-butyldimethylsilyl chloride, triethylamine, 4-dimethylaminopyridine (DMAP) gave aldehyde 13 (93% yield) (Jong, T. T.; Williard, P. G.; Porwoll, J. P., J. Org. Chem., 1984, 49, 735–6). Baeyer-Villiger oxidation of 13 with m-chloroperbenzoic acid (MCPBA) in methylene chloride (70% yield) followed by basic hydrolysis with potassium carbonate (90% yield) and silylation of the resulting phenol with t-butyldimethylsilyl chloride (83% yield) provided trisilyl ether 14. Selective C4 (less hindered site compared with C6) bromination of 14 with N-bromosuccinimide (NBS) in N,N-dimethylformamide (DMF) at 25° C. gave an 67% yield of 4 as the sole product; no C6 isomer 15 was isolated. Interestingly, when the bromination was carried out at 50° C., a 2:1 ratio of 15 and 4 was obtained.

Alternatively, compound 4 was also obtained from the bromination of phenol 16 (obtained from 13 with MCPBA and potassium carbonate) with N-bromosuccinimide (NBS) in DMF to give a 70% yield of bromide 17. Silylation of 17 with t-butyldimethylsilyl chloride afforded a 99% yield of 4.

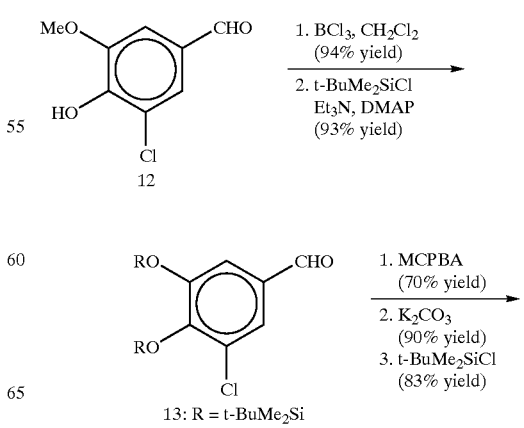

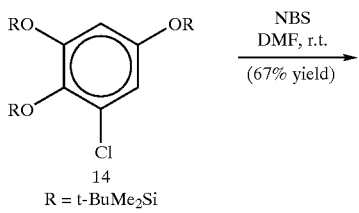

14
R = t-BuMe₂Si

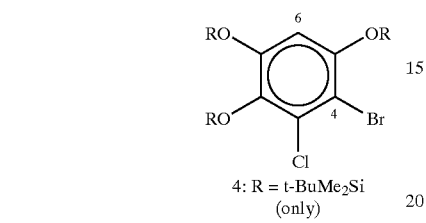

4: R = t-BuMe₂Si
(only)

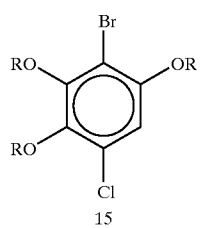

15
When the NBS reaction was carried out at 50° C., a 2:1 ratio of 15 & 4 was obtained

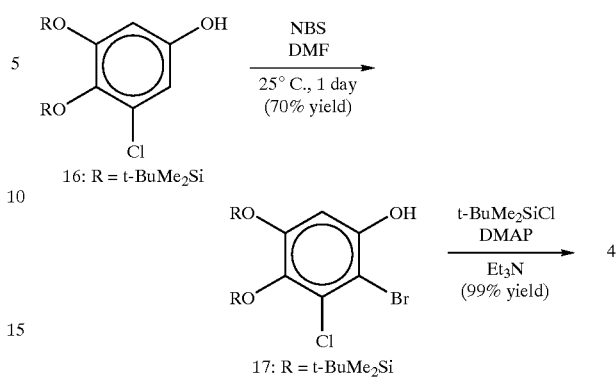

16: R = t-BuMe₂Si

17: R = t-BuMe₂Si

Scheme 3 shows a procedure for preparing compounds embraced by Formulae I and II from enantiopure A-B fragment 3 and D-ring fragment 4. Treatment of 4 with 2 equiv of t-BuLi in diethyl ether at −78° C. followed by aldehyde 3 afforded a mixture of two stereoisomers at C6a, 18 (45% yield) and 19 (9.1% yield). Removal of the silyl ether protecting groups of 18 and 19 separately gave compound 1 (82% yield) and compound 2 (81.4% yield), respectively. Spectral data of compound 2 was identical with those reported (Nasu, S. S.; Yeung, B. K. S.; Hamann, M. T.; Scheuer, P. J.; Kelly-Borges, M.; Goins, K., J. Org. Chem. 1995, 60, 7290–7292).

Scheme 3

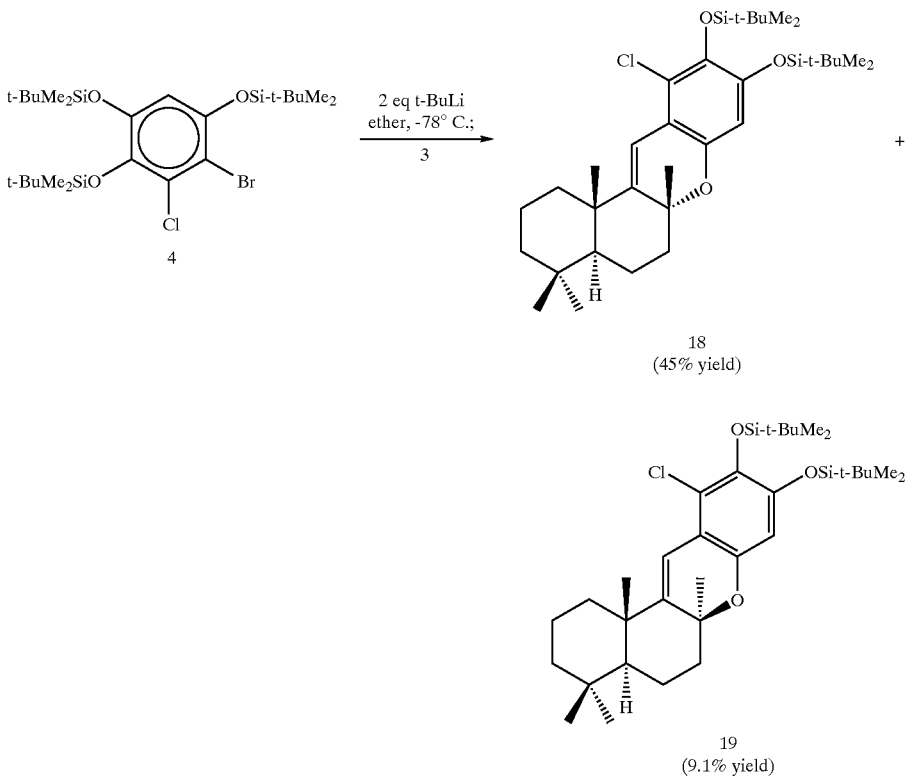

18
(45% yield)

19
(9.1% yield)

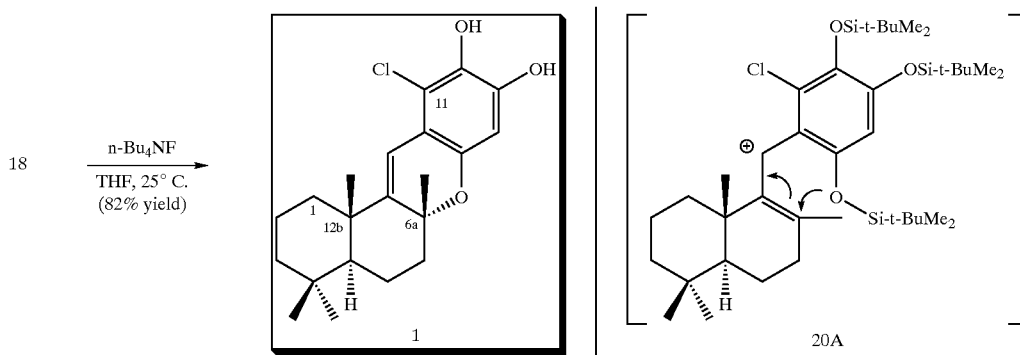

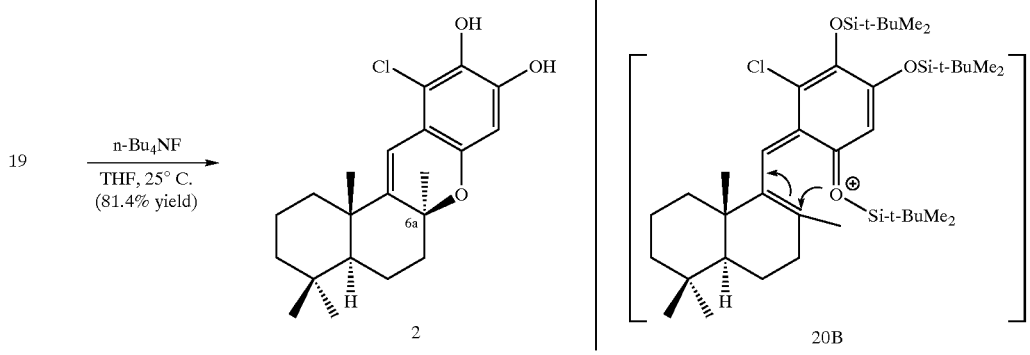

Scheme 4 shows the preparation of compounds embraced by Formulae III, IV, and VI. Selective hydrogenation of 18 with 1 atmosphere of hydrogen in the presence of palladium/carbon in ethanol gave a 99% yield of tetracyclic pyran 21 as a single diastereomer (Scheme 4a). Removal of the silyloxy protecting group of 21 with tetra-n-butylammonium fluoride in THF afforded an 83% yield of diol 22.

Oxidation of diol 22 with pyridinium dichromate (PDC) in dichloromethane gave a mixture of quinones 23 and 24 in a ratio of 6:1. Quinone structures 23 and 24 were assigned based on $^1$H NMR spectrum.

Similarly, hydrogenation of 19 with 1 atmosphere of hydrogen and palladium/carbon (90% yield) followed by desilylation with tetra-n-butylammonium fluoride in THF (31% yield) and oxidation with pyridinium dichromate afforded (+)-chloropuupehenone (27) in 50% yield.

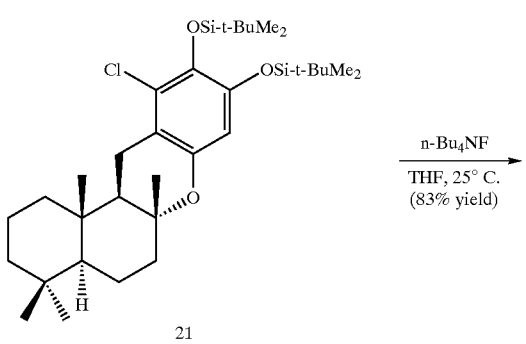

Scheme 4

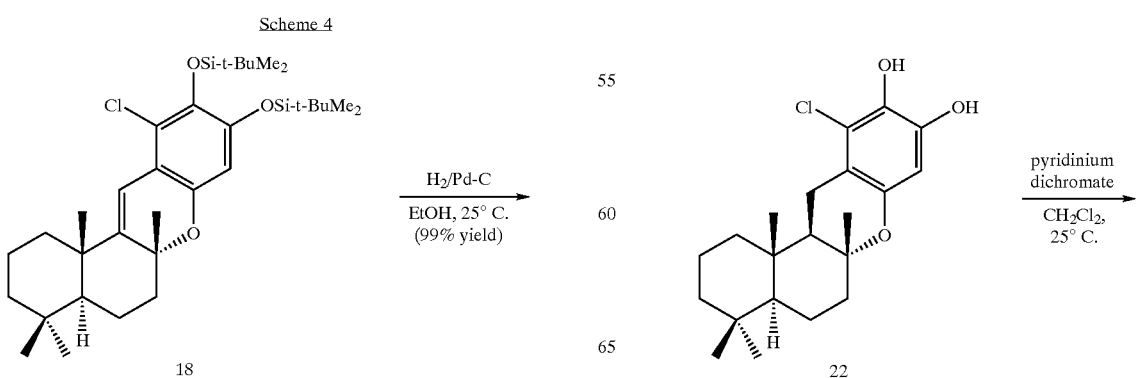

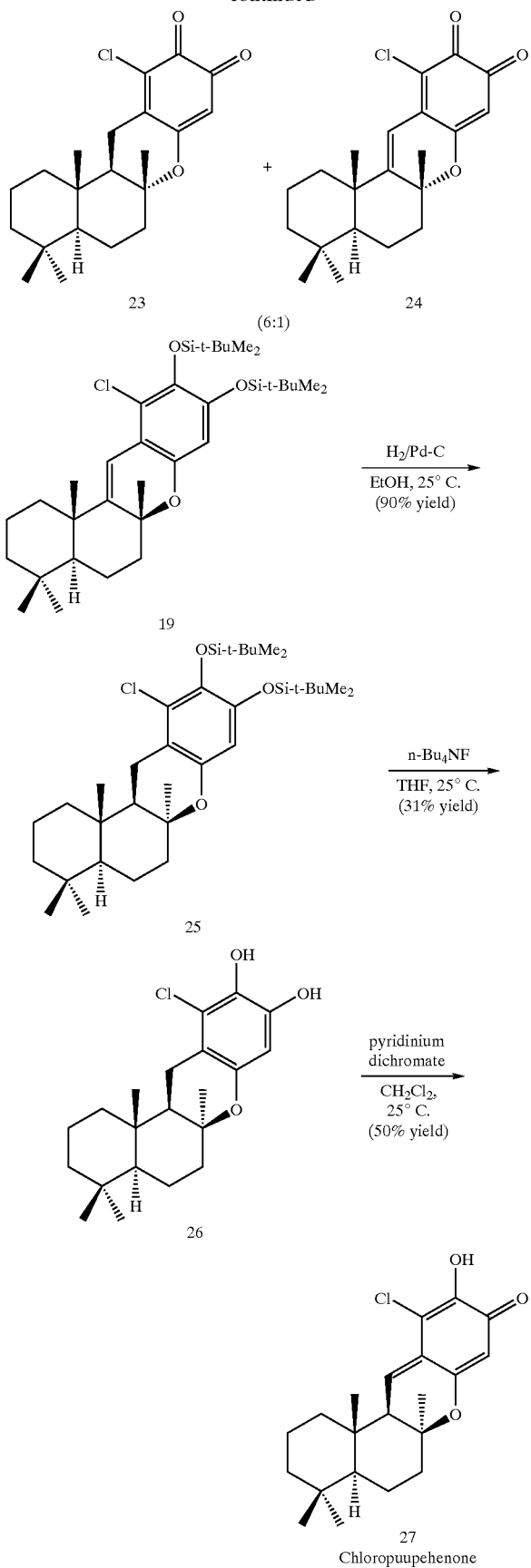

Schemes 5 and 6 show a procedure for preparation of C6a-S tetracyclic pyran compounds embraced by Formulae IV and V. Scheme 5 shows the preparation of (1R,4aS,6aS)-2,5,5,8a-tetramethyl-1,4,4a,5,6,7,8,8a-octahydronaphthalene-1-carboxaldehyde (33) and (1R,4aS, 6aS)-2-Methylene-5,5,8a-trimethyl-1,2,3,4,4a,5,6,7,8,8a,-decahydronaphthalene-1-carboxaldehyde (35). Reduction of aldehyde 10 with lithium aluminum hydride in diethyl ether at 0° C. produced a 97% yield of diol 28. Silylation of the less hindered primary alcohol of 28 with t-butyldimethylsilyl chloride and imidazole in DMF gave alcohol 29 (98% yield). Elimination of 29 with methanesulfonyl chloride (MsCl) and triethylamine in dichloromethane afforded a mixture of alkenes 30 and 31 (1:1; 90% yield), which were separated by silica gel column chromatography. Desilylation of 30 with tetra-n-butylammonium fluoride in THF (88% yield) followed by oxidation with Dess-Martin Periodinane in dichloromethane provided aldehyde 33 (67% yield). Similarly, silyl ether 31 was converted to aldehyde 35 under similar reaction conditions.

Scheme 5

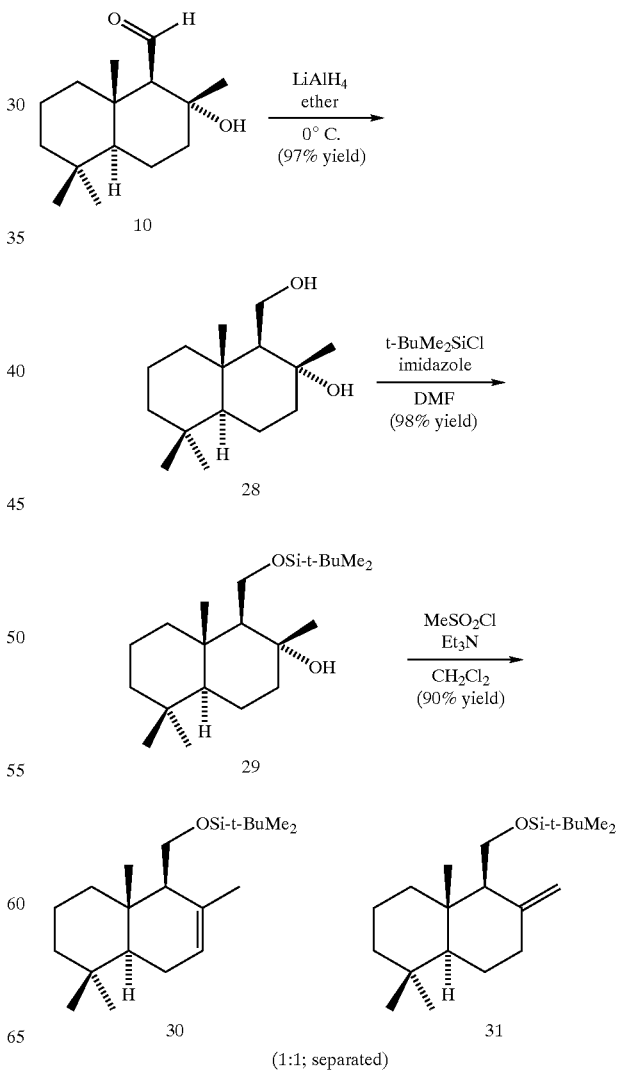

Scheme 6

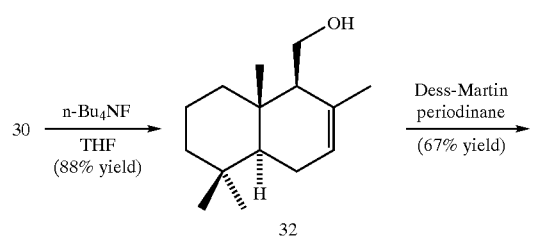

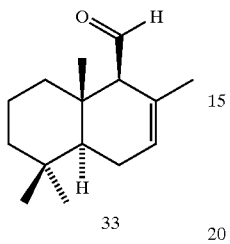

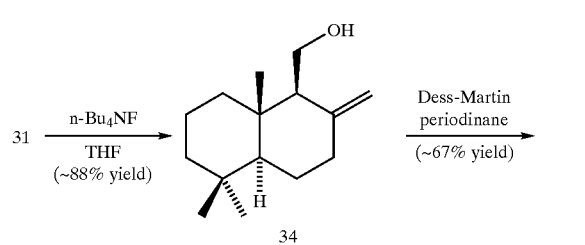

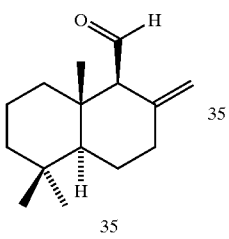

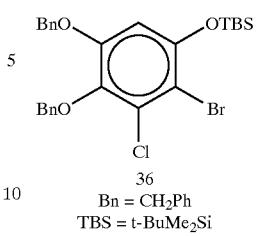

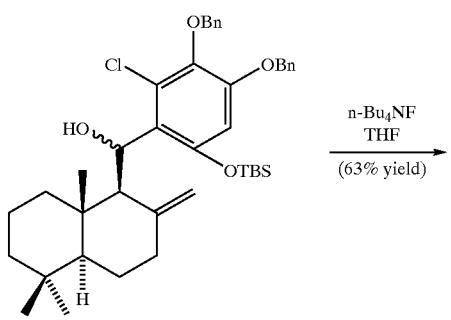

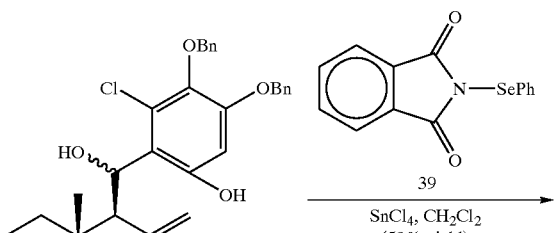

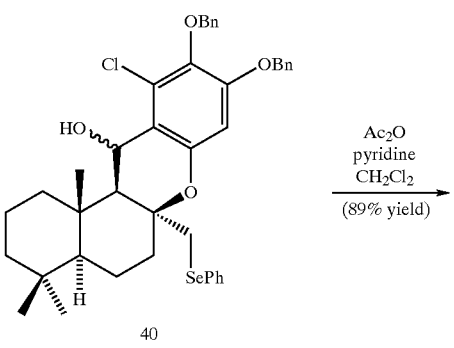

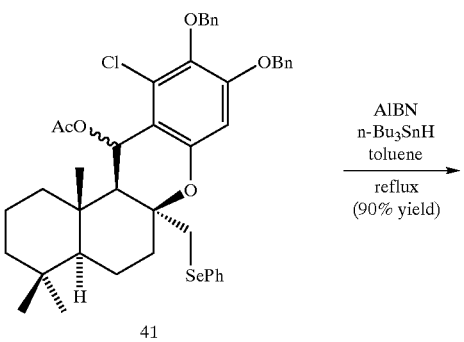

Referring to synthetic Scheme 6, Bromide 36 was synthesized from the dibenzylation of 3,4-dihydroxy-5-chlorobenzaldehyde (see Scheme 2) with NaH and benzyl chloride in THF followed by a similar reaction sequence described for the synthesis of 4 from 13. Treatment of bromide 36 with 1.1 equivalent of t-butyllithium in diethyl ether at −78° C. followed by 1 equivalent of aldehyde 35 gave alcohol 37 (62% yield), which was desilylated with n-Bu$_4$NF in THF to give alcohol 38 (63% yield). Ring closure of 38 with phenylselenylphthalimide and tin tetrachloride in dichloromethane afforded tetracyclic pyran 40 (50% yield) with the C6a-S configuration. The phenylselenyl reagent approaches C6a exo double bond from the opposite face of C12a alkyl group and C7 oxygen attacks the carbocation from the opposite side of the selenium ion to give 40 as the major product. Acetylation of 40 with acetic anhydride and pyridine in dichloromethane (89% yield) followed by removal of the selenyl function with AIBN (2,2'-azobisisobutyronitrile) and tri-n-butyltin hydride in refluxing toluene gave pyran 42 (90% yield). Removal of the benzyl ether protecting group of 42 with 1 atmosphere of hydrogen and palladium-carbon in methanol provided diol 26, which has identical proton NMR spectrum as that obtained in Scheme 4.

-continued

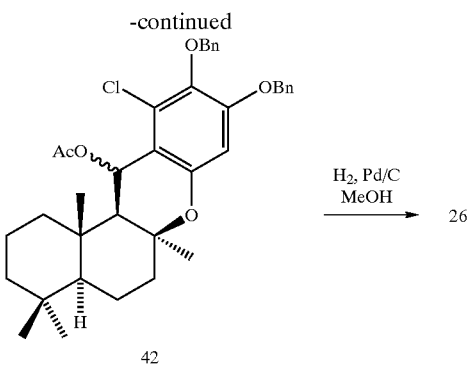

EXAMPLES

Nuclear magnetic resonance spectra were obtained at 400 MHz for $^1$H and 100 MHz for $^{13}$C in deuteriochloroform, and reported in ppm. Infrared spectra are reported in wavenumbers (cm$^{-1}$). Elemental analysis data were obtained from Desert Analytics, Tucson, Ariz. USA, and are reported as % C and % H. Mass spectra were taken from a Hewlett Packard 5890A Series II, GC-MS. Davisil silica gel, grade 643 (200~425 mesh), was used for the flash column chromatographic separation. Tetrahydrofuran and diethyl ether were distilled over sodium and benzophenone before use. Methylene chloride was distilled over CaH$_2$ and toluene and benzene were distilled over LiAlH$_4$. Chemicals and reagents were purchased either from Aldrich Chemical Company or Fisher Chemical Company, and were used without further purification.

Example 1

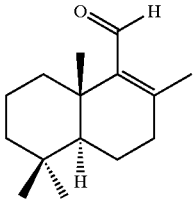

(4aS,8aS)-3,4,4a,5,6,7,8,8a-Octahydro-2,5,5,8a-tetramethylnaphthalene-1-carboxaldehyde Step 1: Preparation of (1S,3aR,5aS,9aS,9bR)-1-Hydroxy-dodecahydro-3a,6,6,9a-tetramethylnaphtho[2,1-b]furan-2-one (6) and (1R,3aR,5aS,9aS,9bR)-1-Hydroxy-dodecahydro-3a,6,6,9a-tetramethylnaphtho[2,1-b]furan-2-one (7)

To a cold (−78° C.) solution of 1.02 mL (7.79 mmol) of diisopropylamine in 40 mL of THF under argon, was added 6.36 mL (7.19 mmol) of n-BuLi (1.6 M in hexane). The solution was stirred at −78° C. for 1 h, and a solution of 1.50 g (5.99 mmol) of (+)-sclareolide 5 in 20 mL of THF was added via cannula dropwise. After the solution was stirred at −78° C. for 1 h, the solution was added to a 5.10 g (0.012 mol) of MoO$_5$.pyridine.HMPA, and stirred for 30 minutes. The mixture was diluted with saturated aqueous Na$_2$SO$_3$, extracted three times with ethyl acetate, and the organic layer was washed with water, and brine, dried (Na$_2$SO$_4$), concentrated, and column chromatographed on silica gel using a mixture of hexane:ether (9:1) as an eluent to give 1.045 g (65.6% yield) of compound 6 and 0.195 g (12% yield) of compound 9 along with 0.296 g (20% recovery) of 5. Compound 6: $[\alpha]^{22}_D$=+97.1° (c 0.01, CHCl$_3$); $^1$H NMR (CDCl$_3$) δ 4.48 (d, J=12Hz, 1H, CHO, axial), 2.06 (d, J=12Hz, 1H, C9b-axial H), 1.95~1.06 (m, 11H), 1.38 (s, 3H, Me), 1.03 (s, 3H, Me), 0.88 (s, 3H, Me), 0.84 (s, 3H, Me); $^{13}$C NMR (CDCl$_3$) δ 179.0 (s, C=O), 83.5, 68.7, 64.2, 56.4, 42.3, 39.4, 39.3, 36.9, 33.4, 33.2, 23.5, 21.1, 20.7, 18.1, 15.9. Compound 7: $[\alpha]^{22}_D$=−19.1° (c 0.01, CHCl$_3$); $^1$H NMR (CDCl$_3$) δ 4.37 (dd, J=5.6, 3.2Hz, 1H, CHO, equatorial), 2.32 (d, J=3.2Hz, 1H, OH), 2.06 (d, J=12Hz, 1H), 1.89~0.98 (m, 10H), 1.69 (s, 3H, Me), 1.21 (s, 3H, Me), 0.87 (s, 3H, Me), 0.85 (s, 3H, Me); $^{13}$C NMR (CDCl$_3$) δ 177.6 (s,C=O), 88.8, 70.2, 62.6, 57.8, 42.4, 39.8, 38.7, 37.3, 27.1, 25.2, 21.1, 20.8, 18.3, 17.3.

Step 2: Preparation of 1-(1S-1,2-Dihydroxyethyl)-(1R,2R,4aS,8aS)-decahydro-2,5,5,8a-tetramethylnaphthalen-2-ol (8S) and (1S,3aR,5aS,9aS,9bR)-Dodecahydro-3a,6,6,9a-tetramethylnaphtho[2,1-b]furan-1,2-diol (9S)

The following representative method describes the reduction of 6 and 7 to triol 8 and lactol 9. A solution of 0.90 g (3.4 mmol) of 6 in 20 mL of THF under argon, was added 0.66 g (17.3 mmol) of LiAlH$_4$, and the mixture was stirred for 4 h at 25° C. To it, 60 mL of water and 16 mL of 1 N HCl were added, and the solution was extracted with diethyl ether three times (50 mL each). The combined ether extracts were washed with brine, dried (MgSO$_4$), concentrated, and column chromatographed on silica gel using a gradient mixture of hexane and ethyl acetate as an eluent to give 0.65 g (71% yield) of triol 8S and 0.273 g (30% yield) of lactol 9S. Compound 8S: $[\alpha]^{22}_D$=−7.2° (c 0.008, CH$_3$OH); $^1$H NMR (CDCl$_3$) δ 4.53 (m, 1H, CHO), 4.08 (dd, J=10, 8Hz, 1H, CH$_2$O), 3.64 (dd, J=10, 4Hz, 1H, CH$_2$O), 1.95 (d, J=4Hz, 1H), 1.70~1.01 (m, 11H), 1.43 (s, 3H, Me), 1.10 (s, 3H, Me), 0.90 (s, 3H, Me), 0.82 (s, 3H, Me); $^{13}$C NMR (CDCl$_3$) δ 82.9, 75.2, 71.8, 68.8, 48.7, 42.4, 38.4, 36.3, 34.9, 33.7, 33.2, 28.3, 23.0, 21.9, 20.0, 18.5. Compound 9S (as a mixture of 2 diastereomers at C2): $^1$H NMR (CDCl$_3$) δ 5.38 (broad s, 1H), 5.33 (s, 1H), 4.35 (t, J=5Hz, 1H), 2.5 (broad s, 1H, OH), 1.9~0.9 (m, 12H), 1.49 (s, 3H, Me), 1.19 (s, 3H, Me), 0.86 (s, 3H, Me), 0.84 (s, 3H, Me).

For the 8R isomer, 1-(1R-1,2-Dihydroxyethyl)-(1R,2R,4aS,8aS)-decahydro-2,5,5,8a-tetramethylnaphthalen-2-ol (8R): $^1$H NMR (CDCl$_3$) δ 3.87 (m, 1H, CHO), 3.68 (dd, J=11, 3Hz, 1H, CH$_2$O), 3.42 (dd, J=11, 8Hz, 1H, CH$_2$O), 3.15 (broad s, 3H, OH), 1.80~0.8 (m, 12H), 1.54 (s, 3H, Me), 0.99 (s, 3H, Me), 0.87 (s, 3H, Me), 0.81 (s, 3H, Me). For the 9R isomer, (1R,3aR,5aS,9aS,9bR)-Dodecahydro-3a,6,6,9a-tetramethylnaphtho[2,1-b]furan-1,2-diol (9S): (as a mixture of 2 diastereomers at C2). $^1$H NMR (CDCl$_3$) δ 5.32 (d, J=6Hz, 1H, CHO of 1 diastereomer), 5.22 (d, J=3Hz, 1H, CHO of 1 diastereomer), 4.36~4.10 (m, 2H, CHO of 2 diastereomers), 2.80 (broad s, 4H, OH for 2 diastereomers), 1.90~0.9 (m, 24H for 2 diastereomers), 1.34 (s, 3H, Me), 1.16 (s, 3H, Me), 0.97 (s, 3H, Me), 0.95 (s, 3H, Me), 0.87 (s, 6H, 2Me), 0.83 (s, 6H, 2Me); $^{13}$C NMR (CDCl$_3$) δ 94.5, 79.2, 73.1, 70.8, 64.3, 62.9, 60.6, 57.1, 56.9, 42.5, 40.8, 40.4, 39.9, 37.0, 36.8, 33.8, 33.3, 25.3, 25.2, 24.6, 21.6, 21.3, 20.8, 18.4, 16.4, 16.2.

Step 3: Preparation of (1R,2R,4aS,8aS)-Decahydro-2-hydroxy-2,5,5,8a-tetramethylnaphthalene-1-carboxaldehyde (10)

To a solution of 0.65 g (2.4 mmol) of a mixture of triol 8S and 8R in 25 mL of benzene under argon was added 1.3 g (2.9 mmol) of lead tetraacetate. After stirring at 25° C. for 4 h, the mixture was diluted with diethyl ether, the organic layer was washed with water, and brine, dried (MgSO$_4$), concentrated, and column chromatographed on silica gel using a gradient mixture of hexane and diethyl ether as eluent to give 0.516 g (90% yield) of aldehyde 10. $[\alpha]^{22}_D$=+ 31.9° (c 0.0075, CHCl$_3$); $^1$H NMR (CDCl$_3$) δ 10.06 (d, J=3Hz, 1H, CHO), 2.93 (broad s, 1H, OH), 2.15 (d, J=3Hz, 1H, C1-H), 1.8~0.9 (a series of m, 11H), 1.20 (s, 3H, Me), 1.17 (s, 3H, Me), 0.90 (s, 3H, Me), 0.86 (s, 3H, Me); $^{13}$C NMR (CDCl$_3$) δ 208.3, 72.9, 71.4, 55.3, 42.9, 41.8, 39.9, 37.5, 33.5, 30.5, 25.4, 21.5, 20.0, 18.3, 17.7.

Step 4: Preparation of (4aS,8aS)-3,4,4a,5,6,7,8,8a-Octahydro-2,5,5,8a-tetramethylnaphthalene-1-carboxaldehyde (3)

To a flask equipped with a Dean-Stark apparatus under argon, 10 mg (0.042 mmol) of aldehyde 10, 10 Ml of toluene, and 3 mg (0.017 mmol) of p-toluenesulfonic acid were added. After the solution was reflux for 2 h, the solution was cooled to 25° C., diluted with saturated aqueous sodium bicarbonate, and extracted three times with ethyl acetate. The combined extracts were washed with brine, dried (MgSO4), concentrated, and column chromatographed on silica gel using a gradient mixture of hexane and ethyl acetate as eluent to give 7.2 mg (78% yield) of aldehyde 3.14. In a larger-scale synthesis of 3, the product was distilled under reduced pressure to give colorless oil; bp. 60° C./3 mm Hg (to eliminate trace amount of water), and the distilled product was used in next step. $[\alpha]^{22}_D$=+52° (c 1, CHCl$_3$); $^1$H NMR (CDCl$_3$) d 10.04 (s, 1H, CHO), 2.55 (d, J=13Hz, 1H), 2.26 (dd, J=8, 4 Hz, 1H), 2.03 (s, 2H, Me), 1.70~1.40 (m, 6H), 1.18 (s, 3H, Me), 1.17~0.91 (m, 2H), 0.90 (s, 3H, Me), 0.86 (s, 3H, Me); $^{13}$C NMR (CDCl$_3$) d 192.8 (C=O), 153.7 (C=C), 143.9 (C=C), 51.8, 41.8, 37.8, 36.7, 36.4, 33.6, 33.5, 33.2, 21.8, 20.4, 19.1, 18.5.

Example 2

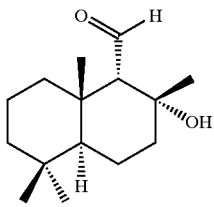

Preparation of (1R,2R,4aS,8aS)-Decahydro-2-hydroxy-2,5,5,8a-tetramethylnaphthalene-1-carboxaldehyde Step 1: Preparation of (1R,2R,4AS,8aS)-Decahydro-2-formyloxy-2,5,5,8a-tetramethylnaphthalene-1-carboxaldehyde (11)

To a solution of 0.30 g (1.1 mmol) of lactols 9S and 9R in 15 mL of benzene under argon was added 0.60 g (1.3 mmol) of lead tetraacetate. After the mixture was stirred at 25° C. for 4 h, it was diluted with diethyl ether, the organic layer was washed with water, and brine, dried (MgSO$_4$), concentrated, and column chromatographed on silica gel using a gradient mixture of hexane and diethyl ether as eluent to give 0.25 g (85% yield) of aldehyde 11. $[\alpha]^{22}_D$=− 54.4° (c 0.25, CHCl$_3$); $^1$H NMR (CDCl$_3$) δ 9.98 (d, J=4Hz, 1H, CHO), 7.92 (s, 1H, OCHO), 2.55 (dd, J=9.6, 3.2Hz, 1H, C4a-H), 2.49 (d, J=4Hz, 1H, C1-H), 1.85 (s, 3H, Me), 1.84~0.90 (m, 10H), 1.18 (s, 3H, Me), 0.89 (s, 3H, Me), 0.83 (s, 3H, Me); $^{13}$C NMR (CDCl$_3$) δ 204.2 (C=O), 160.1 (C=O), 85.9, 68.9, 55.1, 41.7, 40.0, 39.9, 39.1, 33.4, 22.3, 21.6, 21.5, 20.0, 18.1, 17.2.

Step 2: Preparation of (1R,2R,4aS,8aS)-Decahydro-2-hydroxy-2,5,5,8a-tetramethylnaphthalene-1-carboxaldehyde (10)

5-Chloro-3,4-dihydroxybenzaldehyde was prepared according to the procedure of Jong et al. (J. Org. Chem. 1984, 49, 735–6). To a solution of 0.350 g (1.10 mmol) of formyloxy 11 in 20 mL of methanol was added 0.181 g (1.32 mmol) of potassium carbonate. After the solution was stirred at 0° C. for 2 h, the solution was diluted with water and extracted three times with diethyl ether. The combined ether extract was washed with brine, dried (MgSO$_4$), concentrated, and column chromatographed on silica gel using a gradient mixture of hexane and ether as eluent to give 0.241 g (92% yield) of aldehyde 10.

Example 3

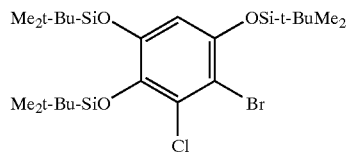

Preparation of 5-Bromo-6-chloro-1,2,4-tris-(t-butyldimethylsilyloxy)benzene

Step 1: Preparation of 3-Chloro-4-hydroxy-5-methoxybenzaldehyde (12)

Compound 12 was prepared according to the procedure of Hann et al. (J. Am. Chem. Soc. 1927, 49, 535–7). To a solution of 2.50 g (16.4 mmol) of vanillin in 15 mL of glacial acetic acid was added chlorine gas through a glass tubing over 30 minutes (with a slow gas flow) at 25° C. White solid product was collected by filtration, washed with 50 mL of hexane, and dried in vacuo to give 2.033 g of 12. The acetic acid filtrate was again treated with chlorine gas as above for 30 minutes to give another 0.659 g of 12. A total of 2.691 g (88% yield) of 12 was obtained. The white solids were used in next step without purification. $^1$H NMR (CDCl$_3$) δ 10.04 (s, 1H, OH), 9.76 (s, 1H, CHO), 7.56 (d, J=1.6 Hz, 1H, Ar), 7.37 (d, J=1.6Hz, 1H, Ar), 3.91 (s, 3H, OMe); $^{13}$C NMR (CDCl$_3$) δ 190.5 (C=O), 149.0 (s, 2C), 128.2 (s), 125.6 (d), 120.1 (s), 109.2 (d), 56.3 (q).

Step 2: Preparation of 5-Chloro-3,4-dihydroxybenzaldehyde

To a solution 2.00 g (10.7 mmol) of benzaldehyde 12 in 20 mL of dichloromethane under argon at 0° C. was added 1.20 mL (11.8 mmol) of boron tribromide. The solution was stirred at 0° C. for 0.3 h and 25° C. for 4 h, diluted with 40 mL of methanol, and the solvents were removed on a rotary evaporator (the trimethylborate was removed). To it was added 40 mL of methanol and methanol and trimethyl borate were removed by evaporation on a rotary evaporator, and this process was repeated three times. The residue was diluted with dichloromethane and filtered and washed with a small amount of dichloromethane to give 1.722 g (94% yield) of pure 5-chloro-3,4-dihydroxybenzaldehyde. This material was used in next step without purification. $^1$H NMR (CDCl$_3$) δ 10.43 (s, 2H, OH), 9.70 (s, 1H, CHO), 7.42 (d, J=2.0Hz, 1H, C6-H), 7.22 (d, J=2.0Hz, 1H, C2-H); $^{13}$C NMR (DMSO-d$_6$) δ 190.6 (C=O), 148.3 (s), 146.9 (s), 128.4 (d), 124.2 (d), 120.3 (s), 112.5 (s).

Step 3: Preparation of 3,4-bis(t-Butyldimethylsilyloxy)-5-chlorobenzaldehyde (13)

To a solution of 1.68 g (9.70 mmol) of 5-chloro-3,4-dihydroxybenzaldehyde and 0.212 g (2.80 mmol) of 4-dimethylaminopyridine (DMAP) in 20 mL of dichloromethane under argon at 0° C. were added 9.80 mL (68.0 mmol) of distilled triethylamine and 4.40 g (59.2 mmol) of t-butyldimethylsilyl chloride. The reaction mixture was stirred at 0° C. for 1 h and 25° C. for 3 h, 100 mL of saturated aqueous NH$_4$Cl was added, and extracted three times with diethyl ether (80 mL each). The combined extracts were washed with 60 mL of brine, dried (MgSO$_4$), concentrated, and column chromatographed on silica gel using a gradient mixture of hexane and diethyl ether as eluent to give 3.64 g (93% yield). $^1$H NMR (CDCl$_3$) δ 6 9.77 (s, 1H, CHO), 7.50 (d, J=2.0 Hz, 1H, C6-H), 7.27 (d, J=2.0 Hz, 1H, C2-H), 1.04 (s, 9H, t-Bu), 0.98 (s, 9H, t-Bu), 0.26 (s, 6H, Me), 0.23 (s, 6H, Me); $^{13}$C NMR (CDCl$_3$) δ 189.3 (C=O), 149.5 (s), 149.2 (s), 130.3 (s), 127.8 (s), 125.7 (d), 118.8 (d), 26.1 (q, 3C, t-Bu), 26.0 (q, 3C, t-Bu), 18.7 (s, 2C, t-Bu), −3.4 (q, 2C, Me), −3.6 (q, 2C, Me). Anal. Calc for C$_{19}$H$_{33}$ClO$_3$Si$_2$: C, 56.90; H, 8.29. Found: C, 56.62; H, 8.41.

Step 4: Preparation of 3,4-bis-(t-Butyldimethylsilyloxy)-5-chlorophenyl Formate

To a solution of 1.73 g (4.30 mmol) of 13 in 15 mL of dichloromethane under argon was added 2.03 g (6.50 mmol) of 55% m-chloroperbenzoic acid (MCPBA). After refluxing for 10 h, the solution was diluted with 30 mL of water and extracted three times with diethyl ether (50 mL each). The combined extracts were washed twice with saturated aqueous NaHCO$_3$ (30 mL each), 30 mL of water, and 30 mL of brine, dried (MgSO$_4$), concentrated, and column chromatographed on silica gel using hexane as eluent to give 1.24 g (70% yield) of 3,4-bis-(t-butyldimethylsilyloxy)-5-chlorophenyl formate. $^1$H NMR (CDCl$_3$) δ 8.22 (s, 1H, CHO), 6.79 (d,J=3.2 Hz, 1H), 6.58 (d,J=3.2 Hz, 1H), 1.03 (s, 9H, t-Bu), 0.96 (s, 9H, t-Bu), 0.22 (s, 6H, Me), 0.19 (s, 6H, Me); $^{13}$C NMR (CDCl$_3$) δ 159.0 (s, C=O), 148.8 (s), 143.0 (s), 142.4 (s), 127.1 (s), 115.5 (d), 113.1 (d), 26.2 (q, 6C, t-Bu), 18.8 (s, 2C, t-Bu), −3.3 (q, 2C, Me), −3.6 (q, 2C, Me).

Step 5: Preparation of 1,2,5-tris-(t-Butyldimethylsilyloxy)-3-chlorobenzene (14)

To a mixture of 1.028 g (2.65 mmol) of 3,4-bis-(t-butyldimethylsilyloxy)-5-chlorophenol, 0.600 g (4.00 mmol) of t-butyldimethylsilyl chloride, and 0.048 g (0.40 mmol) of 4-dimethylaminopyridine in 10 mL of dichloromethane under argon at 25° C. was added 1.30 mL (9.26 mmol) of triethylamine. After stirring at 25° C. for 10 h, the mixture was diluted with 30 mL of water and extracted three times with diethyl ether (50 mL each). The combined extracts were washed with 30 mL of brine, dried (MgSO4), concentrated, and column chromatographed on silica gel using a gradient mixture of hexane and diethyl ether as eluent to give 1.100 g (83% yield) of 14. $^1$H NMR (CDCl3) d 6.49 (d, J=2.8 Hz, 1H, Ar, C4-H), 6.30 (d, J=2.8 Hz, 1H, C6-H), 1.04–0.97 (broad s, 27H, t-Bu), 0.18 (s, 6H, Me), 0.175 (s, 12H, Me); $^{13}$C NMR (CDCl$_3$) d 149.3 (s), 148.6 (s), 138.6 (s), 126.8 (s), 114.6 (d), 112.1 (d), 26.3 (q, t-Bu), 25.9 (q, t-Bu), 18.9 (s), 8.8 (s), −3.5 (q, 2C, Me), −3.4 (q, 2C, Me), −4.3 (q, 2C, Me). Anal. Calcd for C$_{24}$H$_{47}$ClO$_3$Si$_3$: C, 57.27; H, 9.41. Found: C, 57.37; H, 9.55.

Step 6: Preparation of 5-Bromo-6-chloro-1,2,4-tris-(t-butyldimethylsilyloxy)benzene (4)

A mixture of 0.650 g (1.30 mmol) of 14 and 0.276 g (1.60 mmol) of N-bromosuccinimide (NBS) in 10 Ml of DMF under argon was stirred at 25° C. for 5 days. The reaction mixture was diluted with 30 Ml of water, extracted three times with diethyl ether (50 Ml each), and the combined extracts were washed with 30 Ml of brine, dried (MgSO$_4$), concentrated, and column chromatographed on silica gel using a gradient mixture of hexane and diethyl ether as eluent gave 0.506 g (67% yield) of bromide 4. $^1$H NMR (CDCl$_3$) δ 6.41 (s, 1H, Ar, C3-H), 1.03 (s, 9H, t-Bu), 1.02 (s, 9H, t-Bu), 0.97 (s, 9H, t-Bu), 0.23 (s, 6H, Me), 0.22 (s, 6H, Me), 0.18 (s, 6H, Me); $^{13}$C NMR (CDCl$_3$) δ 147.3 (s), 147.2 (s), 139.4 (s), 128.3 (s), 111.1 (d), 108.4 (s), 29.9 (q, t-Bu), 26.3 (q, t-Bu), 26.2 (q), 26, 18.9 (s), 18.6 (s), −3.3 (q, Me), −3.4 (q, Me), −3.5 (q, Me), −4.0 (q). Anal. Calcd for C$_{24}$H$_{46}$BrClO$_3$Si$_3$: C, 49.51; H, 7.96. Found: C, 49.78; H, 8.11.

Example 4

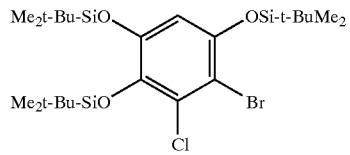

5-Bromo-6-chloro-1,2,4-tris-(t-butyldimethylsilyloxy)benzene

Step 1: Preparation of 3,4-bis-(t-Butyldimethylsilyloxy)-5-chlorophenol (16)

To a solution of 1.236 g (2.97 mmol) of 3,4-bis-(t-butyldimethylsilyloxy)-5-chlorophenyl formate in 10 mL of methanol was added 2.05 g (15.0 mmol) of potassium carbonate at 25° C. The solution was stirred for 30 min., diluted with 35 mL of water, and extracted three times with diethyl ether (50 mL each). The combined extracts were washed with brine, dried (MgSO$_4$), and concentrated to give 1.028 g (90% yield) of 3,4-bis-(t-butyldimethylsilyloxy)-5-chlorophenol. $^1$H NMR (CDCl$_3$) d 6.45 (d, J=2.8 Hz, 1H), 6.31 (d, J=2.8 Hz, 1H), 1.00 (s, 9H, t-Bu), 0.93 (s, 9H, t-Bu), 0.18 (s, 6H, Me), 0.15 (s, 6H, Me); $^{13}$C NMR (CDCl3) d 149.7 (s), 148.9 (s), 137.7 (s), 126.9 (s), 109.8 (d), 107.8 (d), 26.3 (q, 3C), 26.2 (q, 3C), −3.6 (q, 2C, Me), −3.4 (q, 2C, Me). Anal. Calcd for C$_{18}$H$_{33}$ClO$_3$Si$_2$: C, 55.57; H, 8.55. Found: C, 55.39; H, 8.87.

Step 2: Preparation of 2-Bromo-3-chloro-4,5-bis-(t-butyldimethylsilyoxy)phenol (17)

A solution of 0.050 g (0.12 mmol) of 16 and 0.023 g (0.12 mmol) of NBS in 2 mL of DMF under argon was stirred at 25° C. for 1 day. The reaction mixture was diluted with 30 mL of water, extracted three times with diethyl ether (40 mL each), and the combined extracts were washed with brine (30 mL), dried (MgSO$_4$), and concentrated to give 0.042 g (70% yield). This material was used in next step without purification. $^1$H NMR (CDCl$_3$) δ 6.53 (s, 1H, Ar, C6-H), 1.03 (s, 9H, t-Bu), 0.96 (s, 9H, t-Bu), 0.22 (s, 6H, Me), 0.17 (s, 6H, Me); $^{13}$C NMR (CDCl$_3$) δ 148.3 (s), 147.4 (s), 138.8 (s), 127.0 (s), 106.9 (d), 102.9 (s), 26.2 (q, t-Bu), 18.8 (s), −3.3 (q, Me), −3.5 (q, Me).

Step 3: Preparation of 5-Bromo-6-chloro-1,2,4-tris-(t-butyldimethylsilyloxy)benzene To a mixture of 0.042 g (0.090 mmol) of 17, 0.016 g (0.11 mmol) of t-butyldimethylsilyl chloride, and 0.003 g (0.010 mmol) of DMAP in 2 mL of dichloromethane under argon at 25° C. was added 0.05 mL (0.260 mmol) of triethylamine. The reaction mixture was stirred for 3 h, diluted with 30 mL of water, and extracted three times with diethyl ether (30 mL each). The combined ether extracts were with 30 mL of brine, dried (MgSO$_4$), and concentrated to give 0.051 g (99% yield) of 4.

Example 5

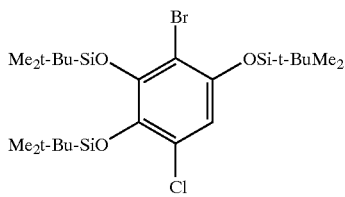

2-Bromo-5-chloro-1,3,4-tris-(t-butyldimethylsilyloxy)benzene

A solution of 0.100 g (0.20 mmol) of 14 and 0.0354 g (0.20 mmol) of NBS in 2 mL of DMF under argon was stirred at 50° C. for 2 day. The solution was diluted with 30 mL of water, extracted three times with diethyl ether (30 mL each), and the combined extracts were washed with brine, dried (MgSO$_4$), concentrated, and column chromatographed on silica gel using a mixture of hexane and diethyl ether (100:1) as eluent to give 31.4 mg (27% yield) of 4 and 62.9 mg (54% yield) of 15. Compound 15: $^1$H NMR (CDCl$_3$) δ 6.54 (s, 1H, Ar, C6-H), 1.03 (s, 18H, t-Bu), 0.97 (s, 9H, t-Bu), 0.23 (s, 12H, Me), 0.17 (s, 6H, Me).

Example 6

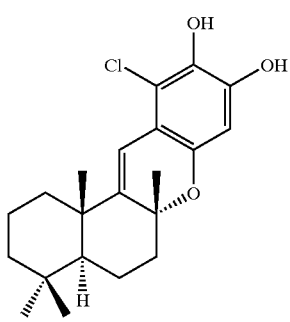

(1)

Step 1: Preparation of (4aS,6aR,12bS)-2H-9,10-bis-(t-Butyldimethylsilyloxy)-11-chloro-1,3,4,4a,5,6,6a,12b-octahydro-4,4,6a,12b-tetramethyl-benzo[a]xanthene (18) and (4aS,6aS,12bS)-2H-9,10-bis-(t-Butyldimethylsilyloxy)-11-chloro-1,3,4,4a,5,6,6a,12b-octahydro-4,4,6a,12b-tetramethyl-benzo[a]xanthene (19)

In a dried flask, 2.600 g (4.50 mmol) of bromide 4 was placed, it was dried by adding 1 mL of freshly distilled toluene (distilled over sodium) followed by evaporation under vacuum, this addition-evaporation of toluene process was repeated, and maintained under argon. To it, 25 mL diethyl ether (freshly distilled over sodium-benzophenone) was added, cooled to −78° C., and 2.7 mL (4.50 mmol) of t-BuLi (1.7 M in pentane) was added via syringe. After stirring at −78° C. for 0.5 h, a solution of 0.820 g (3.70 mmol) of aldehyde 3 (distilled under reduced pressure) in 10 mL of diethyl ether (−78° C.) was added via cannula, and the resulting solution was stirred at −78° C. for 10 min., 25° C. for 1 h (the reaction was monitored by TLC). The reaction solution was diluted with 10 mL of saturated aqueous NH$_4$Cl, extracted three times with diethyl ether, and the combined extracts were washed with water, and brine, dried (MgSO$_4$), concentrated, and column chromatographed on silica gel using a gradient mixture of hexane and toluene and then hexane and ether as eluents to give 0.980 g (45% yield) of 18 and 0.200 g (9.1% yield) of 19. Compound 18: [α]$^{22}_D$=+56° (c 0.033, CHCl$_3$); $^1$H NMR (CDCl$_3$) δ 6.43 (s, 1H, C8-H), 6.28 (s, 1H, C12-H), 2.18 (d, J=12 Hz, 1H), 2.02 (d, J=12 Hz, 1H), 1.90~1.00 (a series of m, 9H), 1.37 (s, 3H, Me), 1.16 (s, 3H, Me), 1.03 (s, 9H, t-BuSi), 0.95 (s, 9H, t-BuSi), 0.92 (s, 3H, Me), 0.87 (s, 3H, Me), 0.21 (s, 3H, MeSi), 0.20 (s, 3H, MeSi), 0.17 (s, 9H, MeSi), 0.16 (s, 3H, MeSi); $^{13}$C NMR (CDCl$_3$) δ 151.3, 147.3, 146.1, 138.1, 123.6, 115.7, 111.7, 107.9,78.0, 52.4,41.8,41.7,39.5, 38.2, 33.8, 33.6, 26.4 (3C, t-Bu), 26.3 (3C, t-Bu), 26.1, 23.7, 21.9, 19.5, 19.1, 18.9, −3.2, −3.46, −3.49, −3.6. Compound 19: [α]$^{22}_D$=+50° (c 0.018, CHCl$_3$); $^1$H NMR (CDCl$_3$) δ 6.39 (s, 1H, C8-H), 6.31 (s, 1H, C12-H), 2.20~0.90 (m, 11H), 1.31 (s, 3H, Me), 1.23 (s, 3H. Me), 1.03 (s, 9H, t-Bu), 0.96 (s, 9H, t-Bu), 0.95 (s, 3H, Me), 0.86 (s, 3H, Me), 0.21 (s, 3H, MeSi), 0.20 (s, 3H, Me), 0.18 (s, 3H, Me), 0.15 (s, 3H, Me); $^{13}$C NMR (CDCl$_3$) δ 151.9, 147.5, 146.0, 138.0, 123.8, 116.5, 111.9, 108.0, 78.0, 52.2, 44.1,42.3, 39.4,39.1, 34.0, 33.0, 31.1, 26.4 (3C, t-Bu), 26.3 (3C, t-Bu), 26.1, 25.6, 25.1, 23.7, 21.4, 19.2, 18.9, 18.8, 17.6, −3.3, −3.4, −3.5, −3.6. Anal. Calcd for C$_{33}$H$_{55}$ClO$_3$Si$_2$: C, 67.02; H, 9.37. Found: C, 67.11; H, 9.16.

2D NOESY spectra were obtained and in compound 18, C6a methyl and C12b methyl have NOE connectivity, however, in compound 19, C6a methyl and C12b methyl have no NOE connectivity.

Step 2: Preparation of(4aS,6aR,12bS)-2H-11-Chloro-1,3,4,4a,5,6,6a,12b-octahydro-4,4,6a,12b-tetramethyl-benzo[a]xanthene-9,10-diol (1)

To a solution of 0.160 g (0.270 mmol) of 18 in 3 mL of THF under argon at 25° C. was added 0.58 mL (0.600 mmol) of tetra-n-butylammonium fluoride (1.0 M in THF). After stirring at 25° C. for 5 min., 0.30 mL of acetic acid was added, the resulting solution was concentrated on a rotary evaporator, and column chromatographed on silica gel using a gradient mixture of hexane and ethyl acetate as eluent to give 0.080 g (82% yield) of 1. [α]$^{22}_D$=+0.11° (c 0.018, CH$_2$Cl$_2$); $^1$H NMR (CDCl$_3$) δ 6.42~6.20 (broad s, 3H, C8H, C12H, and OH), 5.8 (broad s, 1H, OH), 2.18 (d, J=12 Hz, 1H), 2.01 (d, J=12 Hz, 1H), 1.86~0.90 (a series of m, 9H), 1.42 (s, 3H, Me), 1.15 (s, 3H, Me), 0.92 (s, 3H, Me), 0.87 (s, 3H, Me); $^{13}$C NMR (CDCl$_3$) δ 151.3, 147.3, 146.1, 138.1, 123.6, 115.7, 111.7, 107.9, 78.0, 42.3, 41.8, 38.2, 34.0, 33.9, 33.5, 33.0, 21.9, 21.4, 20.9, 19.5, 19.1.

Example 7

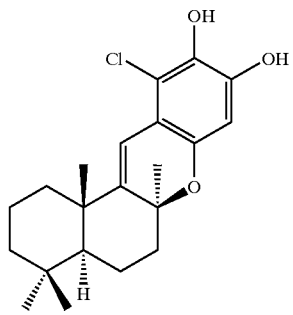

(2)

(4aS,6aS,12bS)-2H-11-Chloro-1,3,4,4a,5,6,6a,12b-octahydro-4,4,6a,12b-tetramethyl-benzo[a]xanthene-9,10-diol To a solution of 60 mg (0.10 mmol) of 19 in 2 mL of THF under argon at 25° C. was added 0.22 mL (0.22 mmol) of tetra-n-butylammonium fluoride (1.0 M in THF). After stirring at 25° C. for 10 min., 0.10 mL of acetic acid was added, the solution was concentrated on a rotary evaporator, and the residue was column chromatographed on silica gel using a gradient mixture of hexane and ethyl acetate as eluent to give 30 mg (81.4% yield) of 2. $[\alpha]^{22}{}_D$=+1.1° (c 0.014, CHCl$_3$); $^1$H NMR (CDCl$_3$) δ 6.38 (s, 1H, C8H), 6.31 (s, 1H, C12H), 5.36 (broad s, 1H, OH), 5.03 (broad s, 1H, OH), 2.20~1.05 (a series of m, 11H), 1.44 (s, 3H, Me), 1.23 (s, 3H, Me), 0.96 (s, 3H, Me), 0.87 (s, 3H, Me); $^{13}$C NMR (CDCl$_3$) δ 151.3, 148.5, 146.1, 133.6, 123.6, 116.5, 110.6, 103.0, 78.0, 43.8, 42.0, 39.1, 33.8, 32.7, 30.8, 30.3, 25.0, 21.2, 20.5, 18.9, 17.2.

Example 8

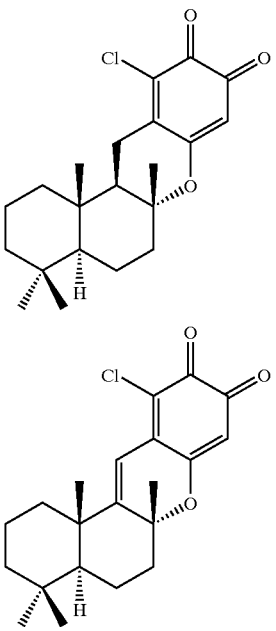

(4aS,6aR,12aR,12bS)-2H-11-Chloro-1,3,4,4a,5,6,6a, 9,10,12,12a,12b-dodecahydro-4,4,6a,12b-tetramethyl-benzo[a]xanthene-9,10-dione (23) and (4aS,6aR,12aR,12bS)-2H-11-Chloro-1,3,4,4a,5,6,6a, 9,10,12b-decahydro-4,4,6a,12b-tetramethyl-benzo[a] xanthene-9,10-dione (24)

Step 1: Preparation of (4aS,6aR,12aR,12bS)-2H-9,10-bis-(t-Butyldimethylsilyloxy)-11-chloro-1,3,4,4a,5,6,6a,12,12a, 12b-decahydro-4,4,6a,12b-tetramethyl-benzo[a]xanthene (21)

A mixture of 0.180 g (0.300 mmol) of compound 18 and 0.400 g of 10% palladium/carbon in 7 mL of distilled ethanol was charged with 1 atmosphere of hydrogen gas (by the use of a hydrogen balloon), and the mixture was stirred at 25° C. for 2 h. The reaction mixture was filtered through a short Celite column, washed the column with ethanol, and the combined filtrate was concentrated, and column chromatographed on silica gel using a gradient mixture of hexane and toluene as eluent to give 0.180 g (99% yield) of 21. $[\alpha]^{22}{}_D$=+35.6° (c 0.008, CHCl$_3$); $^1$H NMR (CDCl$_3$) δ 6.23 (s, 1H, C8H), 2.64 (dd, J=17, 5 Hz, 1H, C12H), 2.33 (dd, J=17, 12 Hz, 1H, C12H), 2.02 (dt, J=12, 3 Hz, 1H), 1.80~1.15 (a series of m, 11H), 1.12 (s, 3H, Me), 1.03 (s, 9H, t-Bu), 0.95 (s, 9H, t-Bu), 0.90 (s, 6H, Me), 0.85 (s, 3H, Me), 0.194 (s, 3H, MeSi), 0.191 (s, 3H, MeSi), 0.17 (s, 3H, MeSi), 0.15 (s, 3H, MeSi); $^{13}$C NMR (CDCl$_3$) δ 147.4, 146.5, 137.4, 126.8, 114.4, 108.2, 76.8, 56.4, 52.2, 42.1, 41.1, 39.4, 37.1, 33.7, 33.4, 26.4 (3C, t-Bu), 26.3 (3C, t-Bu), 25.2, 24.1, 21.8, 20.7, 20.0, 18.9, 18.7, 15.0 –3.2 (MeSi), –3.4, –3.5 (2C). Anal. Calcd for $C_{33}H_{57}ClO_3Si_2$: C, 66.79; H, 9.68. Found: C, 67.15; H, 9.45.

Step 2: Preparation of (4aS,6aR,12aR,12bS)-2H-11-Chloro-1,3,4,4a,5,6,6a,12,12a,12b-decahydro-4,4,6a,12b-tetramethyl-benzo[a]xanthene-9,10-diol (22)

To a solution of 39 mg (0.066 mmol) of 21 in 2 mL of THF under argon at 25° C. was added 0.20 mL (0.20 mmol) of tetra-n-butylammonium fluoride (1 M in THF). The solution was stirred for 30 min., 1 drop of acetic acid was added, the resulting red solution was concentrated to dryness, and column chromatographed on silica gel using a gradient mixture of hexane and ethyl acetate to give 20 mg (83% yield) of diol 22. $^1$H NMR (CDCl$_3$) δ 6.35 (s, 1H, C8H), 5.33 (broad s, 1H, OH), 5.06 (broad s, 1H, OH), 2.61 (d, J=17 Hz, 1H, C12H), 2.34 (m, 1H, C12H), 2.02 (m, 1H), 1.80~0.90 (a series of m, 11H), 1.14 (s, 3H, Me), 0.91 (s, 6H, Me), 0.85 (s, 3H, Me). When the proton NMR spectrum was measured in benzene-d6 solvent, all methyl groups are separated, δ 0.99 (s, 3H, Me), 0.77 (s, 3H, Me), 0.71 (s, 3H, Me), 0.61 (s, 3H, Me). $^{13}$C NMR (C$_6$D$_6$) δ (the aromatic carbons are not well defined and are not described here) 76.6, 55.9, 51.9, 41.9, 41.0, 39.0, 36.8, 33.4, 33.1, 30.0, 21.6, 19.8, 19.1, 18.7, 14.7.

Step 3: (4aS,6aR,12aR,12bS)-2H-11-Chloro-1,3,4,4a,5,6, 6a,9,10,12,12a,12b-dodecahydro-4,4,6a,12b-tetramethyl-benzo[a]xanthene-9,10-dione (23) and (4aS,6aR,12aR, 12bS)-2H-11-Chloro-1,3,4,4a,5,6,6a,9,10,12b-decahydro-4,4,6a,12b-tetramethyl-benzo[a]xanthene-9,10-dione (24)

To a solution of 10 mg (0.027 mmol) of diol 22 in 1 mL of dichloromethane under argon at 25° C. was added 3 mg of pyridinium dichromate (PDC). After stirring for 2 h, the mixture was diluted with a small amount of dichloromethane, filtered through Celite, and concentrated to dryness to give 9.0 mg of a mixture of 23 and 24 in a ratio of 6:1 (obtained from NMR spectrum). $^1$H NMR (CDCl$_3$) δ 6.74 (s, 1H, C12H of 24), 5.95 (s, 1H, C8H of 24), 5.80 (s, 1H, C8H of 23), 2.84 (dd, J=20, 5 Hz, 1H, C12H of 23), 2.50 (dd, J=20, 13 Hz, C12H of 23), 2.11 (dt, J=13, 3 Hz, 1H, 23), 2.22~0.90 (a series of m, 11H of 23 and 11H of 24), 1.33 (s, 3H, Me of 23), 0.93 (s, 3H, Me of 23), 0.92 (s, 3H, Me of 23), 0.85 (s, 3H, Me of 23).

Example 9

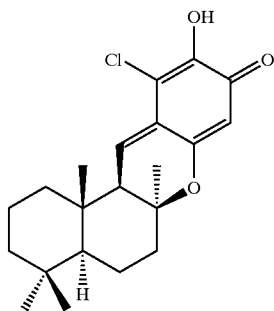

(+)-Chloropuupehenone

Step 1: Preparation of (4aS,6aS,12aR,12bS)-2H-9,10-bis-(t-Butyldimethylsilyloxy)-11-chloro-1,3,4,4a,5,6,6a,12,12a, 12b-decahydro-4,4,6a,12b-tetramethyl-benzo[a]xanthene (25)

A mixture of 0.060 g (0.10 mmol) of compound 19 and 0.080 g of 10% palladium/carbon in 2 mL of distilled ethanol was charged with 1 atmosphere of hydrogen gas (by the use of a hydrogen balloon), and the mixture was stirred at 25° C. for 2 h. The reaction mixture was filtered through Celite, washed with dichloromethane, and the combined filtrate was concentrated, and column chromatographed on silica gel using a gradient mixture of hexane and toluene as eluent to give 0.54 g (90% yield) of compound 25. $[\alpha]^{22}_D$=−35° (c 0.007, CHCl$_3$); $^1$H NMR (CDCl$_3$) δ 6.21 (s, 1H, C8H), 2.75 (d, J=18 Hz, 1H, C12H), 2.64 (dd, J=18, 8 Hz, 1H, C12H), 2.10 (d, J=11 Hz, 1H), 1.85 (d, J=12 Hz, 1H), 1.62~1.10 (a series of m, 10H), 1.11 (s, 3H, Me), 1.03 (s, 9H, t-Bu), 0.95 (s, 9H, t-Bu), 0.89 (s, 3H, Me), 0.81 (s, 3H, Me), 0.64 (s, 3H, Me), 0.20 (s, 3H, MeSi), 0.18 (s, 3H, MeSi), 0.16 (s, 3H, MeSi), 0.157 (s, 3H, MeSi); $^{13}$C NMR (CDCl$_3$) δ 148.9, 146.3, 137.3, 126.0, 114.6, 108.4, 75.4, 55.5, 49.7, 42.1, 40.7, 40.3, 38.6, 33.9, 33.5, 27.1, 26.4 (3C, t-Bu), 26.3 (3C, t-Bu), 22.1, 21.9, 18.9, 18.7, 18.5, 14.1, −3.3 (2C, MeSi), −3.5, −3.6. Anal. Calcd for $C_{33}H_{57}ClO_3Si_2$: C, 66.79; H, 9.68. Found: C, 66.92; H, 9.78.

Step 2: Preparation of (4aS,6aS,12aR,12bS)-2H-11-Chloro-1,3,4,4a,5,6,6a,12,12a,12b-decahydro-4,4,6a,12b-tetramethyl-benzo[a]xanthene-9,10-diol (26)

To a solution of 50 mg (0.084 mmol) of 25 in 2 mL of THF under argon at 25° C. was added 0.25 mL (0.25 mmol) of tetra-n-butylammonium fluoride (1 M in THF). The solution was stirred for 15 min., 1 drop of acetic acid was added, the resulting red solution was concentrated to dryness, and column chromatographed on silica gel using a gradient mixture of hexane and ethyl acetate to give 10 mg (50% yield) of diol 26. $[\alpha]^{22}_D$=+0.22° (c 0.036, CHCl$_3$); $^1$H NMR (CDCl$_3$) δ 6.33 (s, 1H, C8H), 5.20 (broad s, 2H, OH), 2.72 (d, J=17 Hz, 1H, C12H), 2.64 (dd, J=17, 7 Hz, 1H, C12H), 1.84 (d, J=13 Hz, 1H), 1.60~0.90 (a series of m, 11H), 1.12 (s, 3H, Me), 0.89 (s, 3H, Me), 0.81 (s, 3H, Me), 0.67 (s, 3H, Me); $^{13}$C NMR (CDCl$_3$) δ 149.1, 143.1, 133.3, 119.1, 112.4, 103.3, 75.7, 68.2, 55.4, 49.4, 42.1, 40.6, 40.3, 38.5, 33.9, 33.4, 27.1, 22.1, 18.7, 18.4, 14.3.

Step 3: Preparation of (+)-Chloropuupehenone (27)

To a solution of 6.0 mg (0.016 mmol) of 26 in 1 mL of dichloromethane under argon at 25° C. was added 12 mg (0.032 mmol) of PDC. After stirring for 15 min., the solution was filtered through Celite, rinsed with diethyl ether, concentrated and column chromatographed on silica gel using a gradient mixture of hexane and diethyl ether as eluent to give 3.0 mg (50% yield) of chloropuupehenone (27). MS (CI) m/z 363, 362 (M+1 and M+), 211, 173, 84. $^1$H NMR (CDCl$_3$) δ 7.14 (d, J=7 Hz, 1H, C12H), 5.84 (s, 1H, C8H), 2.18 (d, J=7 Hz, 1H, C12aH), 1.80~0.80 (a series of m, 11H), 1.24 (s, 3H, Me), 0.93 (s, 3H, Me), 0.86 (s, 3H, Me), 0.82 (s, 3H, Me); $^{13}$C NMR (CDCl$_3$) δ 180.0 (C=O), 162.7, 144.4, 141.2, 127.7, 125.7, 105.2, 79.3, 54.9, 54.0, 41.8, 41.2, 40.3, 39.2, 33.9, 33.6, 28.2, 22.2, 18.6, 18.3, 15.4.

$^1$H and $^{13}$C NMR spectral data are similar to those reported (Hanann, M. T.; Scheuer, P. J., J. Org. Chem., 1993, 58, 6565–6569).

3-Chloro-4,5-dibenzyloxybenzaldehyde: Anal. Calcd for $C_{21}H_{17}ClO_3$: C, 71.49; H, 4.86. Found: C, 71.24; H, 5.00.

3-Chloro-4,5-dibenzyloxyphenal: Anal. Calcd. For C20H17ClO3: C, 70.49; H, 5.03. Found: C, 70.13; H, 5.11.

4-Bromo-3-chloro-1,2-dibenzyloxy-5-(t-butyldimethylsilyoxy)benzene (36): Anal. Calcd for $C_{26}H_{30}BrClO_3Si$: C, 58.48; H, 5.66. Found: C, 58.81; H, 5.74.

Example 10
Lymphatic Absorption of Cholesterol

Ten male Sprague-Dawley rats (Harlan Sprague Dawley, Inc., Indianapolis, Ind.) weighing 274.3±7.8 grams were housed individually in plastic cages in an environmentally controlled room of illumination (12:12-h light/dark cycle with the dark period from 0330 to 1530), humidity (60–70%), and temperature (22–25° C.) throughout the study. Rats had free access to deionized water and a nutritionally adequate diet (Table 1) containing soybean oil as the fat source and egg white as the protein source. The diet was formulated according to AIN-93G recommendations (In: Trace Elements in Laboratory Rodents (Watson, R. R., ed.), pp. 3–37. CRC Press, Boca Raton, Fla.). Animals were cared for in an animal care facility accredited by the American Association for the Accreditation of Laboratory Animal Care. Rats were maintained in accordance with the policies and guidelines for animal care and use procedures of the Kansas State University Institutional Animal Care and Use Committee.

TABLE 1

Diet composition[1]

| Ingredient | Amount (g/kg) |
| --- | --- |
| Egg white | 200.0 |
| Cornstarch | 396.5 |
| Dextrinized cornstarch | 132.0 |
| Dextrose | 100.0 |
| Cellulose | 50.0 |
| Soybean oil[2] | 70.0 |
| Mineral mix | 35.0 |
| Vitamin mix | 10.0 |
| Biotin (1 mg/g biotin sucrose mix) | 4.0 |
| Choline bitartrate | 2.5 |

[1]Formulated and supplied from Dyets, Bethlehem, PA, according to the recommendations of the AIN.[17,18]
[2]Contained 0.02% tert-butylhydroquinone.

At 6 wk, rats were starved overnight for 17 h but allowed water ad libitum prior to the surgical placement of a lymph cannula and duodenal infusion catheter. The mesenteric lymph duct was cannulated as described in Koo et al., J. Nutr. 131: 717–722 (2001). Briefly, while rats were under anesthesia (2.0% halothane in 2.0 L O$_2$/min delivered via a halothane vaporizer), a midline abdominal incision was made. The superior mesenteric lymph duct was cannulated with polyethylene tubing (SV.3 1 tubing, i.d. 0.50 mm, o.d. 0.80 mm; Dural Plastics, Auburn, Australia). The cannula was fixed in place with ethyl cyanoacrylate glue (Elmer's Products, Columbus, Ohio) and externalized through the right flank. An indwelling infusion catheter (Silastic® laboratory tubing, i.d. 1.0 mm, o.d. 2.2 mm; Dow Coming, Midland, Mich.) was introduced via the gastric fundus into the upper duodenum and secured in place with a purse-string suture (4-0 Silk, Ethicon, Somerville, N.J.) around the fundic incision. The infusion catheter was exteriorized alongside the lymph cannula. After the abdominal incision was closed, the rats were placed in restraining cages and housed in a recovery chamber at 30° C. for postoperative recovery for 22–24 h. During the recovery period, rats were infused continuously with glucose in phosphate buffered saline (PBS) (in mmol/L: 277 glucose, 6.75 Na$_2$HPO$_4$, 16.5 NaH$_2$PO$_4$, 115 NaCl, and 5 KCl; pH 6.7) v infusion catheter at 3.0 mL/h by a syringe pump (Harvard Apparatus, Model 935, South Natick, Mass.) to ensure adequate hydration and nutritional status of the animals.

After postoperative recovery, each rat was infused with a lipid emulsion at 3 mL/h for 8 h via the duodenal catheter in subdued light. The lipid emulsion consisted of 451.8 μmol triolein (95%, Sigma Chemical, St. Louis, Mo.), 33.3 kBq [4-$^{14}$C]-cholesterol ($^{14}$C-CH; specific activity, 1.85 GBq/mmol, American Radiolabeled Chemicals, St. Louis, Mo.), 20.7 μmol cholesterol, 3.1 μmol α-tocopherol (all-rac-dl-α-tocopherol, 97%, Aldrich Chemical, Milwaukee, Wis.) as an antioxidant, and 396.0 μmol sodium taurocholate (Sigma Chemical, St. Louis, Mo.) in 24 mL of PBS buffer, pH 6.5. For half of the rats, the lipid emulsion contained 114.9 μmol compound 1 (41.9 mg). Lipid emulsion was prepared under a gentle $N_2$ stream and subdued light for 55 min using a microprocessor-controlled ultrasonicator equipped with a microtip (XL-2020 Ultrasonic Liquid Processor, Misonix, Farmingdale, N.Y.).

During the duodenal infusion of lipid emulsion, lymph samples were collected hourly in preweighed ice-chilled centrifuge tubes containing 4 mg $Na_2$-EDTA and 30 μg n-propyl gallate (Sigma Chemical, St. Louis, Mo.) as antioxidants. A portion of each lymph sample (100 μL) was mixed with scintillation liquid (ScintiVerse; Fisher Scientific, Fair Lawn, N.J.) and counted by scintillation spectrometry (Beckman LS-6500; Beckman Instruments, Fullerton, Calif.). The total $^{14}C$-radioactivity appearing in hourly lymph volume (the hourly rates of $^{14}C$-CH absorption) was expressed as a percentage of the total radioactivity infused (% dose). All samples were ice chilled and handled in subdued light.

Fatty Acid Analysis

Total lipids were extracted from each lymph sample with a chloroform/methanol mixture. Lipid extracts were then hydrolyzed with methanolic NaOH, and fatty acids were saponified and methylated simultaneously with $BF_3$-methanol. Fatty acid methyl esters (FAME) were analyzed by capillary gas chromatography (Hewlett-Packard, Model 6890, Palo Alto, Calif.) using a HP-INNOWax cross-linked polyethylene glycol phase capillary column (15 m, i.d. 0.53 mm; Resteck Corp., Bellefonte, Pa.).

Statistical analysis

All statistical analyses were performed using PC SAS (SAS Institute, Cary, N.C.). Repeated measures ANOVA and the least significance difference that were used to compare group means. The level of significance was determined at $P < 0.05$.

Results

Figure 2:
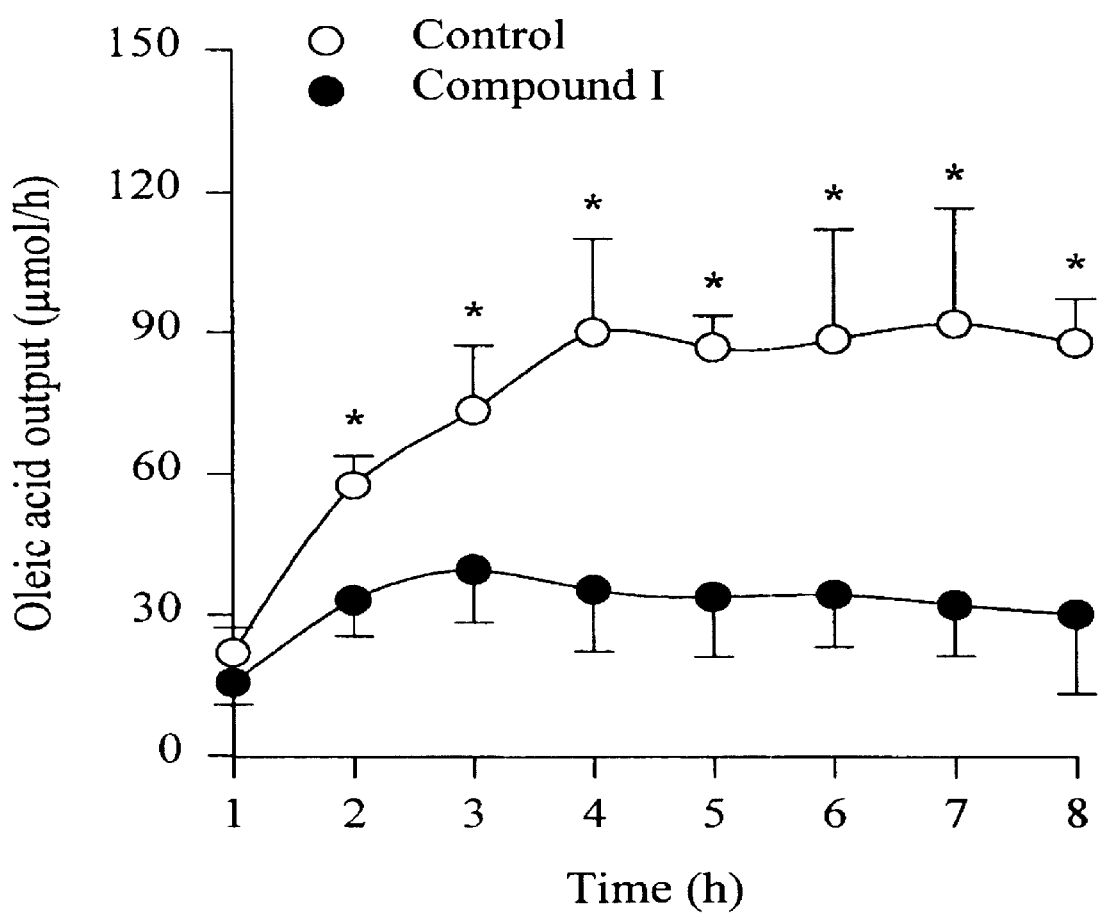
FIG. 2 is a graph showing hourly rates of lymphatic absorption of oleic acid in lymph-cannulated rats. Values are expressed as means±SD, n=5. *Indicates a significant difference between treatments at p<0.05.

Table 2 shows the lymphatic absorption of $^{14}C$—cholesterol and triolein, as well as lymph flow in rats infused for eight hours with lipid emulsion only (control) or containing compound 1. The lymph volume was not significantly different between the two treatments. However, total cholesterol absorption was significantly less in rats infused with compound 1, compared to control rats. In addition, absorption of triolein was significantly less in rats infused with compound 1 compared to control rats. Table 3 and FIG. 1 show the percent dose of $^{14}C$-cholesterol absorbed at hourly intervals. FIG. 2 shows the amount of oleic acid absorbed in the lymph at hourly intervals.

TABLE 2

| Lymph lipid | Control[1] | Compound 1[1] |
|---|---|---|
| Lymph volume, mL/8 h | 18.30 ± 2.43 | 16.59 ± 4.20 |
| $^{14}C$—CH, % dose/8 h | 37.69 ± 1.78 | 10.95 ± 3.29* |
| Oleic acid, μmol/8 h | 598 ± 93 | 253 ± 79* |

[1]Means ± SD, n = 5. *Significantly different from control rats (P < 0.05).

After 8 hours of treatment, the control rats (without drug) had a percent cholesterol absorption of 37.69%, while the treated rats (treated with compound 1) had a percent cholesterol absorption of 10.95%. Under similar test conditions, rats infused with 120.5 mg of green tea catechins per rat per 8 hours had a percent cholesterol absorption of about 10%.

Thus, compound 1 is a more potent inhibitor than green tea catechins, since an inhibitory effect was observed with only 41.9 mg of compound 1. Rats exhibited no gross motor or behavioral abnormalities.

Rats were sacrificed at the day end of the infusion, and the intestine and other organs were dissected and visually examined. No abnormalities were found in any of the organs of either control or treated rats.

TABLE 3

| Time | Control<br>% dose | Compound 1 |
|---|---|---|
| 1 h | 0.16 ± 0.07 | 0.12 ± 0.04 |
| 2 h | 1.84 ± 0.37 | 1.22 ± 0.25* |
| 3 h | 5.31 ± 0.74 | 2.70 ± 0.42* |
| 4 h | 10.16 ± 1.31 | 4.18 ± 0.92* |
| 5 h | 15.66 ± 1.75 | 5.68 ± 1.37* |
| 6 h | 22.14 ± 1.81 | 7.32 ± 1.78* |
| 7 h | 29.79 ± 1.65 | 9.13 ± 2.41* |
| 8 h | 37.69 ± 1.78 | 10.95 ± 3.29* |

[1]Values are means ± SD and cumulative at hourly intervals, n = 5. *Significantly different from control rats (P < 0.05).

Example 11

The inhibitory effect of compound 1 on the activity of cholesterol ester transfer protein (CETP) was measured, using a crude CETP preparation derived from hamster plasma. The results suggested that when the dose of compound 1 exceeded 250 μM, there was an increase in HDL total cholesterol, HDL free cholesterol, and HDL cholesterol ester. These increased HDL levels suggest that compound 1 is an inhibitor of CETP activity in vitro.

Figure 3:
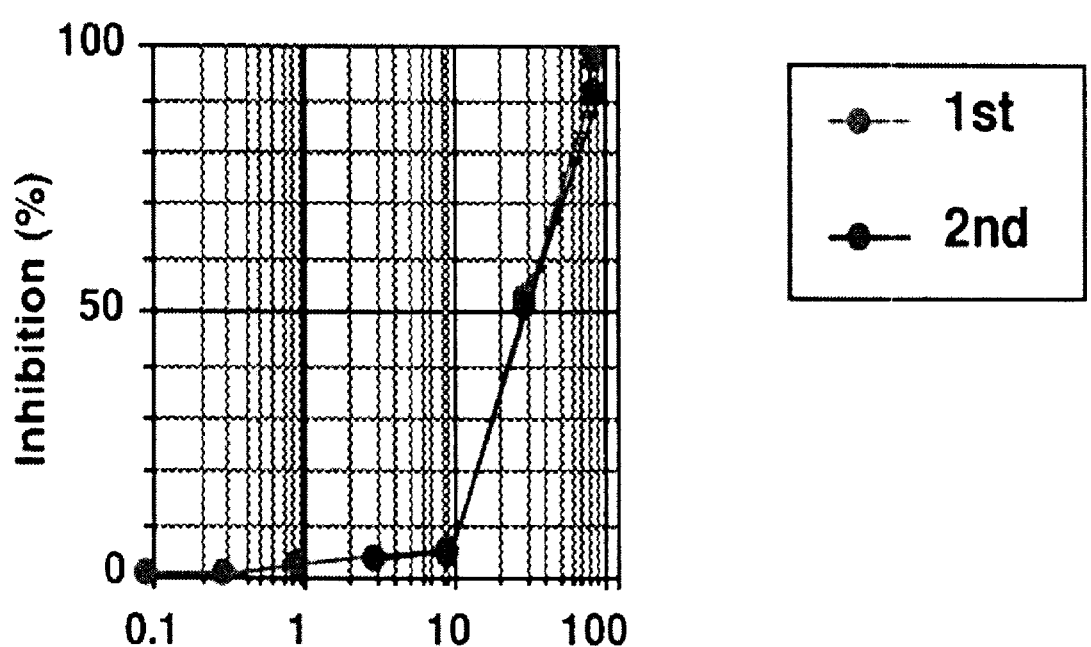
FIG. 3 is a graph showing percent inhibition of cholesterol ester transfer protein (CETP) activity in the presence of various concentrations of compound 24. The results from two replicates of the assay are shown.
Figure 4:
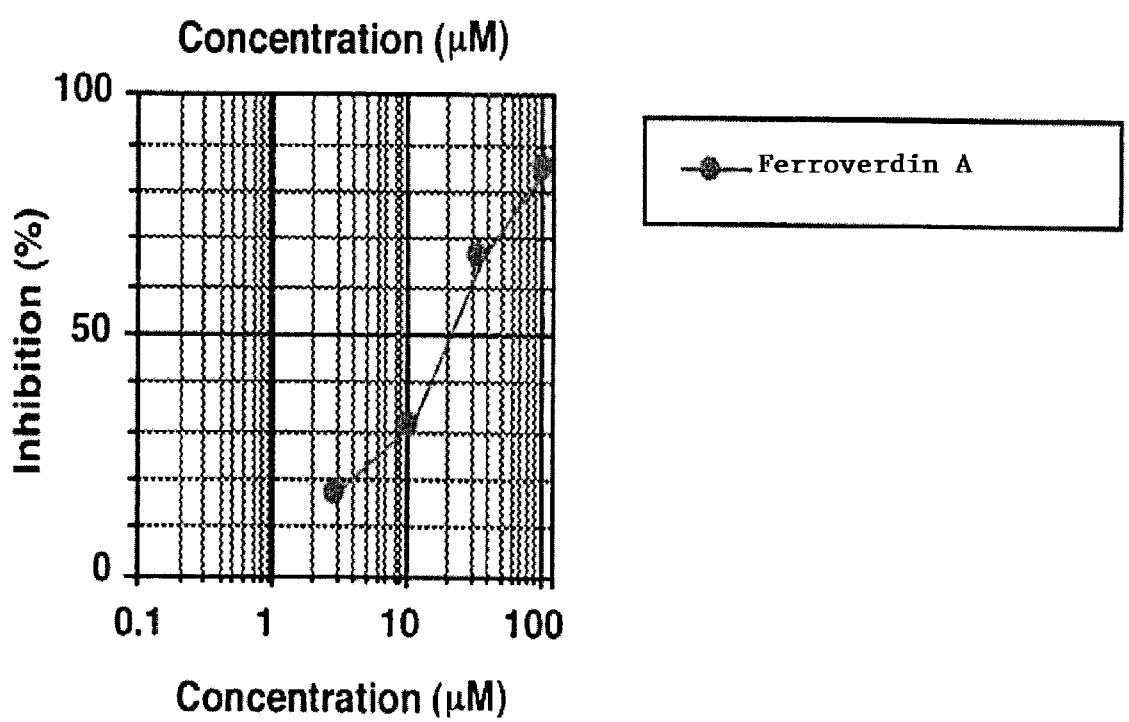
FIG. 4 is a graph showing percent inhibition of CETP activity in the presence of various concentrations of Ferroverdin A.

The effect of compound 24 on inhibition of CETP was tested using a purified CETP preparation. CETP was purified and assayed according to procedures described in Tomada, H.; Tabata, N.; Shinose, M.; Takahashi Y.; Woodruff, H. B.; Omura, S. J. Antibiotics, 52: 1101–1107 (1999). As shown in FIG. 3, there was 50% inhibition (IC50) of CETP activity at 31 μM of compound 24. In comparison, Ferroverdin A, a known CETP inhibitor, resulted in an IC50 of about 22 μM (FIG. 4). The data for compound 24 suggest that compound 24 can inhibit CETP activity in vitro.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula I:

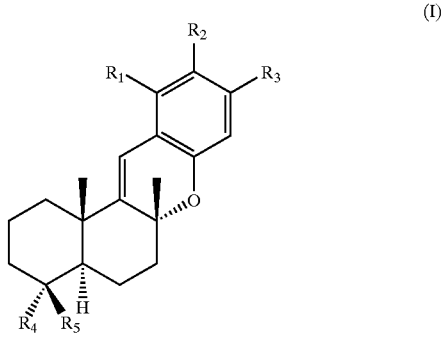

(I)

wherein $R_1$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, or alkylsilyloxy;

$R_2$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, or phenylselenyl, thiol, arylsulfenyl, alkylsulfenyl, arylsulfinyl, or alkylsilyloxy;

$R_3$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, alkylsilyl, phenylselenyl, thiol, arylsulfenyl, alkylsulfenyl, arylsulfinyl, or alkylsilyloxy;

$R_4$ is independently hydrido, alkyl, or hydroxyalkyl; and $R_5$ is independently hydrido, alkyl, or hydroxyalkyl; or a pharmaceutically-acceptable salt thereof.

2. The compound of claim 1, $R_1$ is halo, $R_2$ and $R_3$ are hydroxy, and $R_4$ and $R_5$ are alkyl.

3. The compound of claim 2, wherein $R_1$ is chloro and $R_4$ and $R_5$ are methyl.

4. The compound of claim 1, wherein $R_1$ is halo, $R_2$ and $R_3$ are alkylsilyloxy, and $R_4$ and $R_5$ are alkyl.

5. The compound of claim 4, wherein $R_1$ is chloro, $R_2$ and $R_3$ are OSi-t-BuMe$_2$, and $R_4$ and $R_5$ are methyl.

6. The compound of claim 1, wherein said compound has Formula (24):

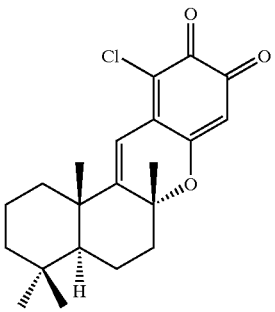

(24)

7. A compound of Formula II:

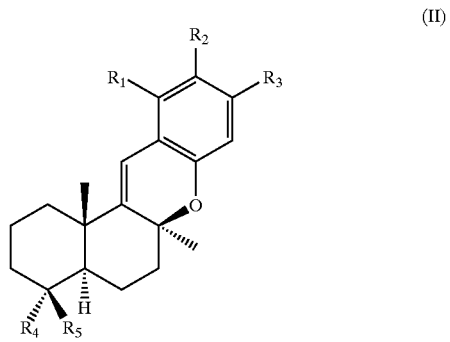

(II)

wherein $R_1$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_2$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_3$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_4$ is independently hydrido, alkyl, or hydroxyalkyl;

$R_5$ is independently hydrido, alkyl, or hydroxyalkyl; or a pharmaceutically-acceptable salt thereof, wherein when $R_1$ is chloro, $R_2$ and $R_3$ are not hydroxy and $R_4$ and $R_5$ are methyl.

8. The compound of claim 7, wherein $R_1$ is halo, $R_2$ and $R_3$ are hydroxy, and $R_4$ and $R_5$ are alkyl.

9. The compound of claim 7, wherein $R_1$ is halo, $R_2$ and $R_3$ are alkylsilyloxy; and $R_4$ and $R_5$ are alkyl.

10. The compound of claim 9, wherein $R_1$ is chloro, $R_2$ and $R_3$ are $OSi\text{-}t\text{-}BuMe_2$, and $R_4$ and $R_5$ are methyl.

11. A compound of Formula III:

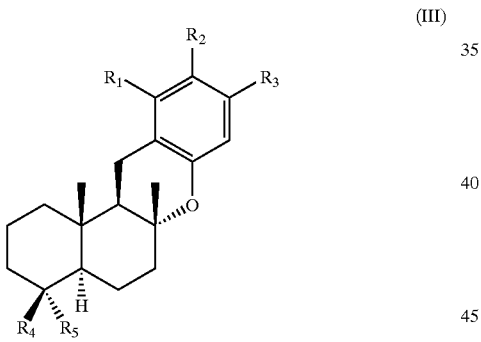

(III)

wherein $R_1$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_2$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_3$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_4$ is independently hydrido, alkyl, or hydroxyalkyl; and $R_5$ is independently hydrido, alkyl, or hydroxyalkyl; or a pharmaceutically-acceptable salt thereof.

12. The compound of claim 11, wherein $R_1$ is halo, $R_2$ and $R_3$ are selected from hydroxy and alkylsilyloxy, and $R_4$ and $R_5$ are alkyl.

13. The compound of claim 11, wherein $R_1$ is chloro, $R_2$ and $R_3$ are hydroxy, and $R_4$ and $R_5$ are methyl.

14. The compound of claim 11, wherein $R_1$ is halo, $R_2$ and $R_3$ are alkylsilyloxy, and $R_4$ and $R_5$ are methyl.

15. The compound of claim 14, wherein $R_1$ is chloro, $R_2$ and $R_3$ are $OSi\text{-}t\text{-}BuMe_2$, and $R_4$ and $R_5$ are methyl.

16. The compound of claim 11, wherein said compound has Formula (23):

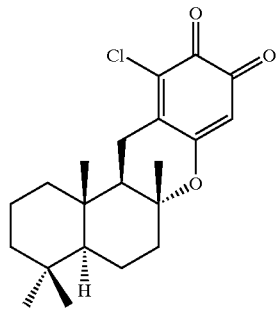

(23)

17. A compound of Formula IV:

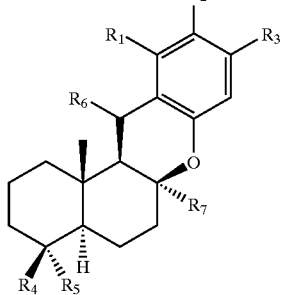

(IV)

wherein $R_1$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

wherein $R_2$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_3$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_4$ is independently hydrido, alkyl, or hydroxyalkyl;
$R_5$ is independently hydrido, alkyl, or hydroxyalkyl;
$R_6$ is independently hydrido, hydroxy, or acyloxy; and
$R_7$ is independently alkyl, or arylselenylalkyl;
or a pharmaceutically-acceptable salt thereof.

18. The compound of claim 17, wherein $R_1$ is halo; $R_2$ and $R_3$ are selected from hydroxy, alkylsilyloxy, or aralkyloxy; $R_4$ and $R_5$ are alkyl; $R_6$ is selected from hydrido, hydroxy, or acyloxy; and $R_7$ is selected from alkyl or arylselenylalkyl.

19. The compound of claim 18, wherein $R_1$ is chloro; $R_2$ and $R_3$ are OSi-t-BuMe$_2$; $R_4$ and $R_5$ are methyl; $R_6$ is hydrido; and $R_7$ is methyl.

20. The compound of claim 18, wherein $R_1$ is chloro; $R_2$ and $R_3$ are hydroxy; $R_4$ and $R_5$ are methyl; $R_6$ is hydrido; and $R_7$ is methyl.

21. The compound of claim 18, wherein $R_1$ is chloro; $R_2$ and $R_3$ are arylalkyloxy; $R_4$ and $R_5$ are methyl; $R_6$ is hydroxy; and $R_7$ is arylselenylalkyl.

22. The compound of claim 18, wherein $R_1$ is chloro; $R_2$ and $R_3$ are arylalkyloxy; and $R_4$ and $R_5$ are methyl; $R_6$ is acyloxy; and $R_7$ is arylselenylalkyl.

23. The compound of claim 18, wherein $R_1$ is chloro; $R_2$ and $R_3$ are arylalkyloxy; $R_4$ and $R_5$ are methyl; $R_6$ is acyloxy; and $R_7$ is methyl.

24. A compound of Formula V:

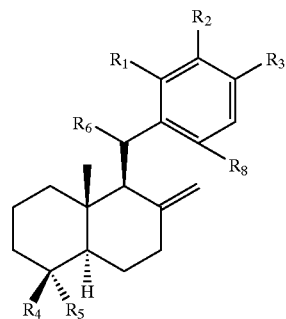

(V)

wherein $R_1$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_2$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_3$ is independently hydrido, halo, alkyl, alkenyl, alkylyl, haloalkyl, hydroxyalkyl, hydroxy, alkoxy, alkoxyalkyl, haloalkoxy, haloalkoxyalkyl, aryl, heterocyclic, heteroaryl, alkylsulfonyl, arylsulfonyl, N-alkylsulfamyl, N,N-dialkylsulfamyl, N-arylsulfomyl, N-alkyl-N-arylsulfamyl, carboxy, carboxyalkyl, alkylcarbonyl, alkylcarbonylalkyl, alkoxycarbonyl, alkoxycarbonylalkyl, amido, N-alkylamido, N-N-dialkylamido, N-monoarylamido, N-alkyl-N-arylamido, N-alkyl-N-hydroxyamido, N-alkyl-N-hydroxyamidoalkyl, amidoalkyl, aminoalkyl, alkylaminoalkyl, amidino, cyanoamidino, heterocycloalkyl, aralkyl, cycloalkyl, cycloalkenyl, alkylthio, alkylsulfinyl, N-alkylamino, N,N-dialkylamino, acyl, acyloxy, aryloxy, acylamino, amino, cyano, nitro, sulfonate, thiol, arylsulfenyl, alkylsulfenyl, arylsulfinyl, alkylsilyl, phenylselenyl, or alkylsilyloxy;

$R_4$ is independently hydrido, alkyl, or hydroxyalkyl;
$R_5$ is independently hydrido, alkyl, or hydroxyalkyl;
$R_6$ is hydroxy; and
$R_8$ is independently hydroxy, or alkylsilyloxy;
or a pharmaceutically-acceptable salt thereof.

25. The compound of claim 24, wherein $R_1$ is halo; $R_2$ and $R_3$ are arylalkyloxy; $R_4$ and $R_5$ are alkyl; $R_6$ is hydroxy; and $R_8$ is selected from hydroxy and alkylsilyloxy.

26. The compound of claim 25, wherein $R_1$ is chloro; $R_2$ and $R_3$ are OBn; and $R_4$ and $R_5$ are methyl; $R_6$ is hydroxy; and $R_8$ is OSi-tBuMe$_2$.

27. The compound of claim 25, wherein $R_1$ is chloro; $R_2$ and $R_3$ are OBn; $R_4$ and $R_5$ are methyl; $R_6$ is hydroxy; and $R_8$ is hydroxy.

28. A method of synthesizing a compound of Formula I:

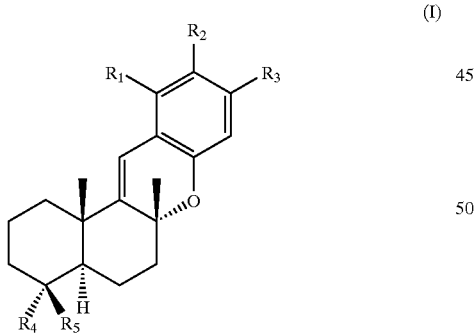

(I)

wherein $R_1$ is chloro, $R_2$ and $R_3$ are hydroxy; and $R_4$ and $R_5$ are methyl, comprising:
a) reacting compound (4),

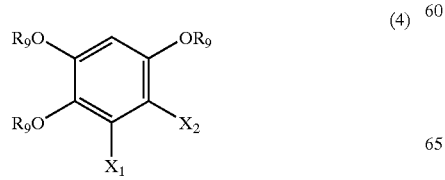

(4)

wherein, $R_9$ is OSi-t-BuMe$_2$, $X_1$ is chloro, $X_2$ is bromo, with compound (3);

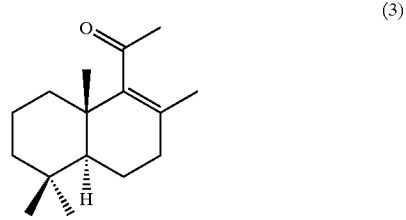

(3)

to form an intermediate compound (18):

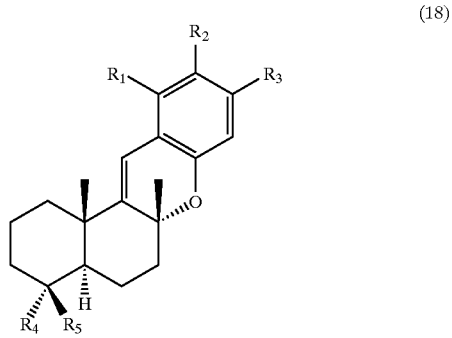

(18)

wherein, $R_1$ is chloro, $R_2$ and $R_3$ are OSi-tBuMe$_2$;
b) isolating said intermediate compound (18); and
c) deprotecting said intermediate compound.

29. A method of synthesizing (+) chloropuupehenone comprising:
a) hydrogenating compound (19) to form compound (25);

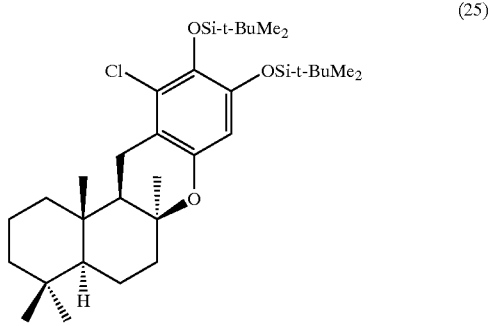

(25)

b) disilylating compound (25) to form compound (26); and

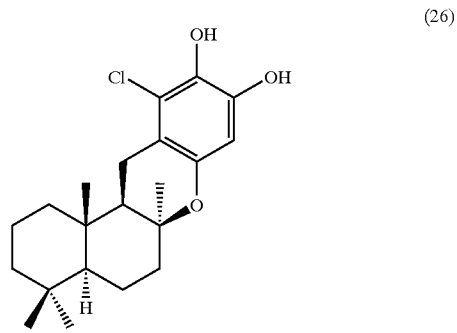

(26)

c) oxidizing compound (26) to form (+) chloropuupehenone (27).

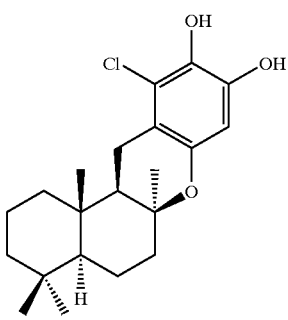

(27)

30. A method for identifying a compound that inhibits lymphatic absorption of cholesterol, comprising:
   a) administering a known amount of cholesterol and a compound of claim 1 to a non-human mammal; and
   b) measuring lymphatic absorption of said known amount of cholesterol, wherein a statistically significant decrease in said cholesterol absorption relative to the lymphatic cholesterol absorption of a corresponding control non-human mammal indicates said compound inhibits lymphatic absorption of cholesterol, and wherein a statistically insignificant change or a statistically significant increase in said cholesterol absorption relative to the lymphatic cholesterol absorption of a corresponding control non-human mammal indicates said compound does not inhibit lymphatic absorption of cholesterol.

31. The method of claim 30, wherein said known amount of cholesterol and said compound are administered in a lipid emulsion.

32. The method of claim 30, wherein said non-human mammal is a rat.

33. The method of claim 32, wherein said non-human mammal is fasted prior to said administering step.

34. A composition comprising a compound of Formula 1:

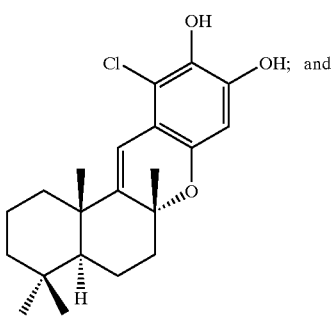

(1)

at least one pharmaceutically-acceptable carrier material.

35. The composition of claim 34, wherein said at least one pharmaceutically-acceptable carrier material is selected from the group consisting of lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, microcrystalline cellulose, sodium starch glycolate, sodium lauryl sulfate, povidone, polyvinylpyrrolidone, and polyvinyl alcohol.

36. The composition of claim 34, wherein said composition is in the form of a capsule or a liquid emulsion.

37. The composition of claim 34, wherein said composition is provided in a controlled release formulation.

38. The composition of claim 37, wherein said composition is provided as a dispersion in hydroxypropylmethyl cellulose.

39. The composition of claim 34, wherein said composition is in a formulation suitable for parenteral administration.

40. The composition of claim 39, wherein said formulation is a lipid emulsion.

41. The composition of claim 34, wherein said composition comprises a diluent selected from the group consisting of polyethylene glycol, propylene glycol, ethanol, corn oil, cottonseed oil, peanut oil, sesame oil, benzyl alcohol.

42. A method of treating a cholesterol-related condition, comprising administering an effective amount of a compound of Formula I to a mammal.

43. The method of claim 42, wherein said cholesterol-related condition is selected from the group consisting of atherosclerosis, hypercholesterolemia, heart attack, gangrene, and stroke.

44. The method of claim 42, wherein said compound is administered orally, intravascularly, intraperitoneally, subcutaneously, intramuscularly, or topically.

45. The method of claim 42, wherein said compound is administered in an amount from about 4 mg/kg to about 4 g/kg of body weight per day.

46. The method of claim 42, wherein said compound is administered as part of a treatment regimen comprising a diet low in cholesterol.

47. The method of claim 42, wherein said compound is administered as part of a treatment regimen comprising administering one or more HMG-CoA reductase inhibitors.

48. The method of claim 42, wherein said mammal is a human.

49. The method of claim 48, wherein said compound is administered for 7 days or more.

50. The method of claim 49, wherein said compound is administered for one year or more.

51. The method of claim 48, wherein said compound is administered in an amount from about 4 mg/kg body weight to about 4 g/kg body weight per day.

* * * * *

UNITED STATES PATENT AND TRADEMARK OFFICE
CERTIFICATE OF CORRECTION

PATENT NO.   : 6,727,277 B1
DATED        : April 27, 2004
INVENTOR(S)  : Duy H. Hua, Sung I. Koo and Sang K. Noh It is certified that error appears in the above-identified patent and that said Letters Patent is hereby corrected as shown below:

Title page,
Item [75], Inventors, please delete "Wrillimantic" and insert -- Willimantic -- therefor; and please delete "US" and insert -- Korea -- therefor;
Item [56], References Cited, OTHER PUBLICATIONS, "Hamann and Scheuer" reference, please delete "Sesquitepene" and insert -- Sesquiterpene -- therefor.

Signed and Sealed this

Fourth Day of January, 2005

JON W. DUDAS
*Director of the United States Patent and Trademark Office*